United States Patent [19]
Venot et al.

[11] Patent Number: 5,872,096
[45] Date of Patent: Feb. 16, 1999

[54] MODIFIED SIALYL LEWIS$^A$ COMPOUNDS

[75] Inventors: Andre P. Venot; Pandurang V. Nikrad; Mohammed A. Kashem, all of Edmonton, Canada

[73] Assignee: Alberta Research Council, Edmonton, Canada

[21] Appl. No.: 325,139

[22] Filed: Oct. 20, 1994

Related U.S. Application Data

[63] Continuation of Ser. No. 887,747, May 22, 1992, abandoned, which is a continuation-in-part of Ser. No. 771,007, Oct. 2, 1991, Pat. No. 5,352,670, which is a continuation-in-part of Ser. No. 714,161, Jun. 10, 1991, abandoned.

[51] Int. Cl.$^6$ .......................... A61K 38/16; A61K 31/70; C07K 9/00; C07M 15/00
[52] U.S. Cl. .................................. 515/8; 514/23; 514/25; 514/60; 530/322; 536/1.11; 536/17.2; 536/17.9; 536/18.7; 536/22.1
[58] Field of Search .......................... 530/322; 536/1.11, 536/17.2, 17.5, 17.6, 17.9, 18.7, 22.1; 514/23, 25, 60, 8

[56] References Cited

U.S. PATENT DOCUMENTS

| | | | |
|---|---|---|---|
| 4,612,132 | 9/1986 | Wollenberg et al. | 252/51.5 A |
| 4,727,136 | 2/1988 | Jennings et al. | 530/395 |
| 5,079,353 | 1/1992 | Ratcliffe et al. | 536/1.11 |
| 5,344,870 | 9/1994 | Ratcliffe et al. | 525/54.2 |
| 5,352,670 | 10/1994 | Venot et al. | 514/54 |
| 5,374,655 | 12/1994 | Kashem et al. | 514/540 |

OTHER PUBLICATIONS

Ichikawa, Y., et al., "Chemical–Enzymatic Synthesis and Conformational Analysis of Sialyl Lewis x and Derivatives" *Am. Chem. Soc.* 114:9283–9298 (1992).
Watkins, W., et al., "Human Fucosyltransferases" *Am. Chem. Soc.*, Ch. 4, pp. 34–61 (1993).
Baba, et al., "Suppression of Cell–Mediated Immune Reactions by Monosaccharides", J. Immunology, vol., 122, No. 3, pp. 838–841 (1979).
Hilgert, et al., "Lentil Lectin Effectively Induces Allotransplantation Tolerance in Mice", *Nature*, 284:273–275 (1980).
Spohr, et al., "Synthetic, Conformational, and Immunochemical Studies of Modified Lewis b and Y Human Blood–Group Determinants to Serve as Probes for the Combining Site of the Lectin IV of *Griffonia simplicifolia*", Carbohydrate Res., 174:211–237 (1988).
Springer, et al., "Sticky Sugars for Selectins", Nature, 349:196–197 (1991).
Barsoum and Davidson, Mol. Immunol., 18:367–372 (1981).
Beyer et al., J. Biol. Chem., 254:12531–12541 (1979).
Conradt et al., Japanese–German Symp. Berlin, 104–105 (1988).
Dumas et al., Bioorg. Med. Chem. Letters, 1:425–428 (1991).
Eppenberger–Castori et al., Glycoconj. J. 6:101–114 (1989).
Fung et al., Cancer Res., 50:4308–4314 (1990).
Hakomori, Adv. Cancer Res., 52:257–331 (1989).
Handa and Nakamuram J. Biochem., 95:1323–1329 (1984).
Henningsson et al., Cancer Immunol. Immunother., 25:231–241 (1987).
Houghton et al., Symposium on Gangliosides and Cancer, pp. 232–237, VCH Publishers (1988).
Howard, in "Towards Better Carbohydrate Vaccines"; Proceedings of a Meeting Organized by the World Health Organization, R. Bell, G. Torrigani, Editors, pp. 221–231, Wiley, Chichester (1987).
Ichikawa et al., Anal. Bio. Chem., 202:215–238.
Irie et al., Symposium on Gangliosides and Cancer, pp. 247–257, VCH Publishers (1988).
Johnson and Watkins, VIIIth Int. Symp. Glycoconjugates, Houston, 2:222–223 (1985).
Kukowska–Latallo et al., Genes & Development, 4:1288–1303 (1990).
Livingston et al., Proc. Natl. Acad. Sci. USA, 84:2911–2915 (1987).
Nakamura and Handa, J. Biochem., (Tokyo) 99:219–226 (1986).
Naor and Galili, Prog. Allergy, 22:107–146 (1977).
Orskov et al., J. Exp. Med., 149:669–685 (1979).
Palcic et al., Carbohydr. Res., 190:1–11 (1989).
Paulson et al., Eur. J. Biochem., 140:523–530 (1984).
Prieels et al., J. Biol. Chem., 256:10456–10463 (1981).
Rearick et al., J. Biol. Chem., 254:4444–4451 (1979).
Ritter, Immunobiology, 182:32–43 (1991).
Sabesan and Paulson, J. Am. Chem. Soc., 108:2068–2080 (1986).
Weinstein et al., J. Biol. Chem., 257:13835–13844 (1982).
Weinstein et al., J. Biol. Chem., 257:13845–13853 (1982).
Baba, et al., *J. Immuno.*, 122(3):838–841 (1979).
Watanabe, *Jpn. J. Cancer Res.*, 76:43–52 (1985).
Phillips, *Science*, 250:1130–1132 (1990).
Walz, et al., *Science*, 250:1132–1135 (1990).
Amvam–Zollo, P., et al. "*Streptococcus pneumoniae* Type XIV Polysaccharide: Synthesis of a Repeating Branched Tetrasaccharide with Dioxa–Type Spacer–Arms", Carbohydrate Research, 150:199–212 (1986).
Aplin, J. D., et al. "*Preparation, Properties, and Applications of Carbohydrate Conjugates of Proteins and Lipids,*" CRC Critical Reviews in Biochemistry, 259–306 (1981).
Barsoum et al., Mol. Immunol., 18:495–550 (1981).
Belkhouya, N., et al. "Halogenation Selective en C–6 de 2–Amino–2–Desoxy–D–Glycopyranoses," 3977–3980 (1991).
Bernotas, R.C., et al. "*Easy assembly for ligands for glycosidase affinity chromatography,*" Biochem. J., 270:539–540 (1990).

(List continued on next page.)

*Primary Examiner*—Elli Peselev
*Attorney, Agent, or Firm*—Burns, Doane, Swecker & Mathis, L.L.P.

[57] ABSTRACT

The present invention is drawn to methods for the synthesis of Lewis$^a$ derivatives modified at the C-2 and/or C-6 position of GlcNAc employing chemo-enzymatic synthesis. The derivatives find use in the treatment and prevention of diseases.

12 Claims, 11 Drawing Sheets

OTHER PUBLICATIONS

Bernstein, M.A., et al. "*A general synthesis of model glycoproteins: coupling of alkenyl glycosides to proteins, using reductive ozonolysis followed by reductive amination with sodium cyanoborohydride,*" Carbohydrate Research, 78:C1–C3 (1980).

Bradford, M.M. "*A Rapid and Sensitive Method for the Quantitiation of Microgram Quantities of Protein Utilizing the Principle of Protein–Dye Binding,*" Analytical Biochemistry, 72:248–254 (1976).

Brandley, B.K., et al. "*Carbohydrate Ligands of the LEC Cell Adhesion Molecules,*" Cell, 63:861–863 (1990).

Brossmer, R., et al. "*Enzymic Synthesis of 5–Acetamido–9–Azido–3, 5, 9–Trideoxy–D–glycero–D–galacto–2–Nonulosonic Acid, A 9–Azido–9–Deoxy Derivative of N–Acetylneuraminic Acid,*" Biochem. and Biophys. Res. Comm., 96:3, 1282–1289 (1980).

Chernyak, A. Y., et al. "*A New Type of Carbohydrate–Containing Synthetic Antigen: Synthesis of Carbohydrate–Containing Polyacrylamide Copolymers having the Specificity of 0:3 and 0:4 Factors of Salmonella,*" Carbohydrate Research, 128:269–282 (1984).

Christian, R., et al. "*On the Side–Chain Conformation of N Acetylneuraminic Acid and its Epimers at C–7, C–8, and C–7,8,*"Christian et al., Carbohydr. Res., 162:1–11 (1987).

Christian, R. "*The Side–Chain Conformations of N–Acetyl–7, 8–, 9–Deoxy–, and 4.7–Dideoxy–Neuraminic Acid and Their Effects on The Activation of CIP:N–Acylneuramininc Acid Cytidylyl–Transferase,*" Carbohy. Res., 194;49–61 (1989).

Conradt, H.S., et al. "Preparation of 9–fluoro–9–deoxy–N–N[214C]acetylneuraminic acid," FEBS, 170:2, 295–300 (1984).

Dahmén, J., et al. "*2–Bromoethyl glycosides: applications in the synthesis of spacer–arm glycosides,*" Carbohydrate Research, 118:292–301 (1983).

Dean, P.D.G., et al. "*Protein Purification using Immobilised Triazine Dyes,*" Journal of Chromatography, 165:301–319 (1979).

Dick, W.E., et al. "*Glycoconjugates of Bacterial Carbohydrate Antigens,*" Contributions to Microbiology and Immunology, 10:48–114 (1989).

Ekborg, G., et al. "*Synthesis of Three Disaccharides for the Preparation of Immunogens bearing Immunodeterminants Known to Occur on Glycoproteins,*" Carbohydrate Research, 110:55–67 (1982).

Feizi, TIBS, 16:84–86 (1991).

Fernandez, V., et al. "*Glycosides of Monoallyl Diethylene Glycol. A New type of Spacer group for Synthetic Oligosaccharides,*" J. Carbohydrate Chemistry, 8(3), 531–537 (1989).

Gokhale, U.B., et al. "*Chemical synthesis of GDP–fucose analogs and their utilization by the Lewis a(1→4) fucosyltransferase,*" Can. J. Chem., 68: 1063–1071 (1990).

Greig, C.G., et al. "*The Preparation of Phenyl 2–Amino–2–deoxy–β–D–glucopyranoside and Some 2–Acylamino–derivatives thereof,*" 879–883 (1961).

Gross, H. J. et al. "*N–Acetyl–4–deoxy–D–neuraminic Acid is Activated and Transferred on to Asialoglycoprotein,*" Glycoconjugate, 4:145–156 (1987).

Gross, H.J., et al. "*Activation and Transfer of Novel Synthetic 9 Substituted Sialic Acids,*" Eur. J. Biochem., 168: 595–602 (1987).

Gross, H.J., et al. "*Enzymatic Introduction of a Fluorescent Sialic Acid into Oligosaccharide Chains of Glycoproteins,*" Eur. J. Biochem., 177: 583–589 (1988).

Handa, S. et al. "*Modification of Sialic Acid Carboxyl Group of Ganglioside,*" J. Biochem., 95: 1323–1329 (1984).

Hagedorn et al., "*6–Thio Sialic Acid And 4–Deoxy Sialic Acid*" XIIIth Carbohydr. Symp., Ithaca (1986)A4.

Hannesian, "*The Reaction of O–benzylideno sugars with N–bromosuccinimide*", 2:86–88 (1966).

Haverkamp, et al. "Improved Synthesis of CMP–Sialates Using Enzymes from Frong Liver and Equine Submandibular Gland," Hoppe–Seyler's Z. Physiol. Chem., 360: 159–166 (1979).

Higa, H. H. "*Sialylation of Glycoprotein Oligosaccharides with N–Acetyl–, N–Glycolyl–, and N–O–Diacetylneuraminic Acids,*" J. of Biol. Chem., 260: 8838–8849 (1985).

Horowitz, The Glycoconjugates, vols. I–V, Pigman, Ed., New York, Academic Press (1977, 1978, 1982, 1983).

Inazu, T., et al. "*New Synthetic Methods and Reagents for Complex Carbohydrates. II. Synthesis of 2–Acylamino–2–deoxy–D–glucopyranose Derivatives by Dimethylphosphinothioic Mixed Anhydride Method,*" Bull. Chem. Soc. Jpn., 611: 4467–4469 (1988).

Kovac, P., et al. "*Synthesis and N.M.R. Spectra of Methyl 2–Deoxy–2–Fluoro–and 3–Deoxy–3–Fluoro–α– and β–D–Glucopyranosides,*" Carbohydrate Research, 169:23–34 (1987).

Lee, R.T., et al. "*Synthesis of 3–(2–Aminoethylthio)Propyl Glycosides,*" Carbohydrate Research, 37: 193–201 (1974).

Lemieux, R.U., et al. "*The Properties of a 'Synthetic' Antigen Relates to the Human Blood–Group Lewis a,*" Journal of the American Chemical Society, 97: 4076–4083 (1975).

Matsumoto, I., et al. "*Derivatization of Epoxy–Activated Agarose with Various Carbohydrates for the Preparation of Stable and High–Capacity Affinity Adsorbents: Their use for Affinity Chromatography of Carbohydate–Binding Proteins,*" Analytical Biochemistry, 116: 103–110 (1981).

Nunez, H. A., et al. "*The Synthesis and characterization of α– and β–L–fucopyranosyl phosphates and GDP fucose,*" Can. J. Chem., 59: 2086–2095 (1981).

Palcic, M.M. "*The Use of Hydrophobic Synthetic Glycosides as Acceptors in Glycosyltransferase Assays,*" Glycoconjugate J., 5:49–63 (1988).

Paulsen, H., et al. "*Synthese Von Oligosaccharid–Determination MitAmid–Spacer Vom Typ Des T–Antigens,*" Carbohydrate Research, 104: 195–219 (1982).

Paulson, J. C., et al. "*Enzymatic Properties of β–D–Galactoside α2→6 Sialyltransferase from Bovine Colostrum,*" The Journal of Biological Chemistry, 252:7, 2363–2371 (1977).

Paulson, "*Interaction of Animal Viruses with Cell Surface Recptors,*" in The Receptors, Conn, Ed., N.Y., Acad. Press, 131–219 (1985).

Petitou, M., et al. "*Synthesis of Heparin Fragments. A Chemical Synthesis of the Pentasaccharide O–(2–Deoxy–2–Sulfamido–6–O–Sulfo–α–D–Glucopyranosyl)–(1→4)–O–(β–D–Glycopyranosyluronic Acid)–(1→4)–O–(2–Deoxy–2–Sulfamido–3,6–Di–O–Sulfo–α–D–Gluco–Pyranosyl)–(1→4)–O–(2–O–Sulfo–α–L–Idopyranosyluronic Acid)–(1→4)–2–Deoxy–2–Sulfamido–6–O–Sulfo–D–Glucopyranose Decasodium Salt, A Heparin Frangment Having High Affinity for Antithrombin III,*" Carboydrate Research, 147: 221–236 (1986).

Petrakova, E., et al. "*Molecular recognition IX.1 The synthesis of the H–type 2 human blood group determinant and congeners modified at the 6–position of the N–acetylglucosamine unit,*" Can. J. Chem., 70: 233–240 (1992).

Piekarska, B., et al. "*A new method for the synthesis of ureido sugars,*" Carbohydrate Research, 203: 302–307 (1990).

Pinto, B.M., et al. "*Preparation of glycoconjugates for use as artificial antigens: A simplified procedure,*" Carbohy. Res., 124: 313–318 (1983).

Rana, S. S., et al. "*Synthesis of Phenyl 2–Acetamido–2–Deoxy–3–O–αL–Fucopyramnosyl–β–D–Glucopyranosidee and Related Compounds,*" Carbohydrate Research, 91: 149–157 (1981).

Reuter, G., et al. "*Suggestions on the Nomenclature of Sialic Acids,*" Glycoconjugate J., 5: 133–135 (1988).

Ritter, G., et al. "*Antibody Response to Immunization With Purified GD3 Ganglioside and GD3 Derivatives* (*Lactones, Amide and Ganglosidol*) *in the Mouse,*" Imm. 182:32–43 (1990).

Sialic Acids in "*Cell Biology Monographs*", Schauer, Ed., vol. 10 (1982).

Schengrund, C., et al. "*Binding of Vibrio cholera Toxin and the Heat labile Enterotoxin of Escherichia coli to $G_{M1}$, Derivatives of $G_{M1}$, and Nonlipid Oligosaccharide Polyvalent Ligands,*" 13233–13237.

Schmidt, R. R., et al. "*Stereospecific Synthesis of α– and β–L Fucopyransyl Phosphates and of GDP–Fucose via Trichloroacetimidate,*" Liebigs Ann. Chem., 121–124 (1991).

Sticher, U., et al. "*Purification of a2,6–sialyltransferase from rat liver by dye chromatography,*" Biochem. J., 353: 577–580 (1988).

Trumtel, M., et al. "*The Synthesis of 2'–Deoxy–β–Disaccharides: Novel Approaches,*" Carbohydrate Research, 191: 29–52 (1989).

Veeneman, G.H., et al. "*An approach towards the synthesis of 1,2–trans glycosyl phosphates via iodonium ion assisted activation of thioglycosides,*" Tetrahedron Lett., 32: 6175–6178 (1991).

Zbiral, E., et al. "*Synthesis of the 4–acetamido–4–deoxy analogue of N–acetylneuraminic acid and its behaviour towards CMP–sialate synthase,*" Carbohydrate Research, 194:C15–C18 (1989).

| $R^2$ | NHAc | $N_3$ | $NH_2$ | NHPr |
|---|---|---|---|---|
| | 7a | 7b | 7c | 7d |
| | 8a | 8b | 8c | 8d |

$R = (CH_2)_8 CO_2 CH_3$
$Pr = COCH_2 CH_3$

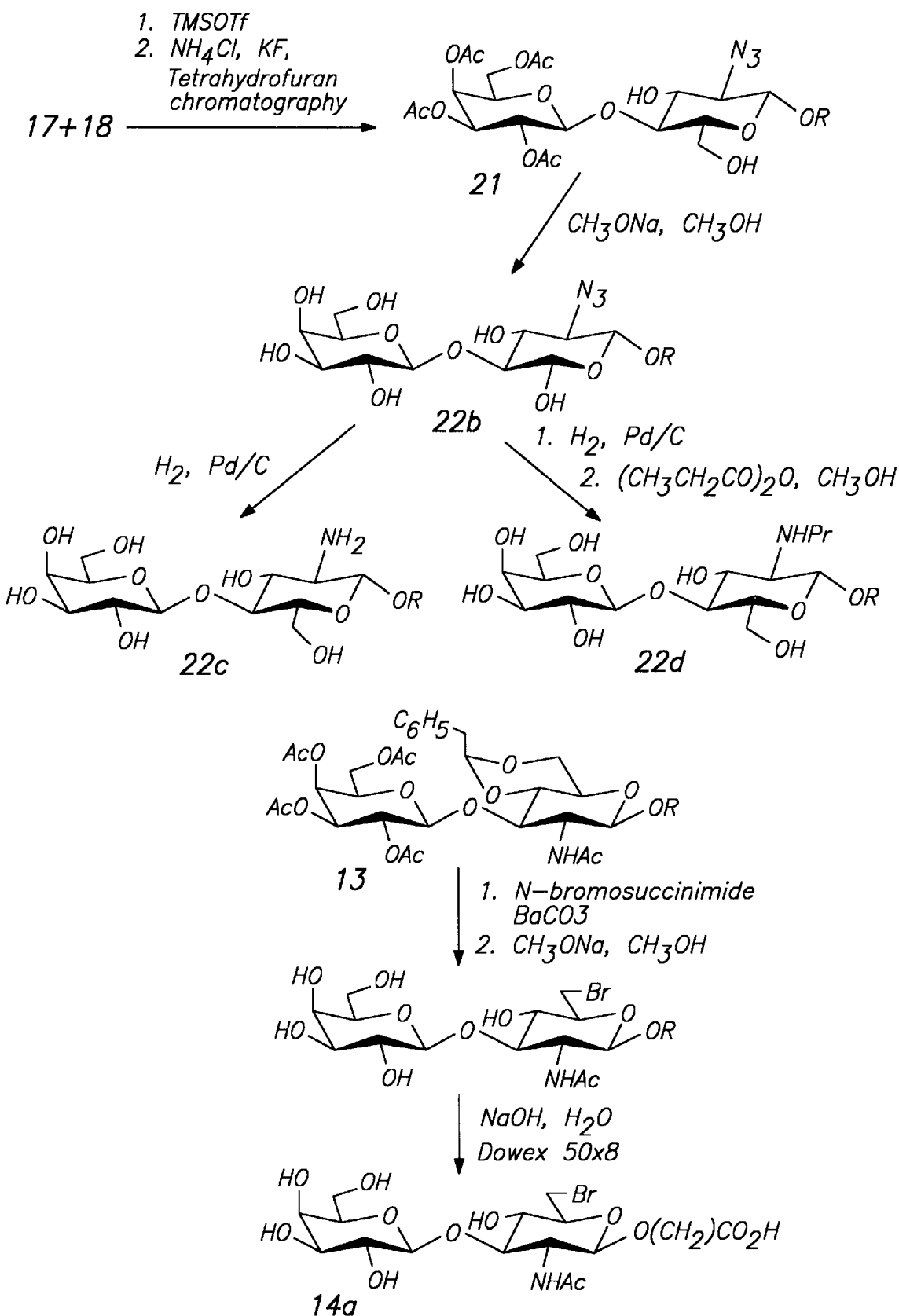
FIG. 4-2      R = $(CH_2)_8CO_2CH_3$

MODIFIED SIALYL LEWIS$^A$ COMPOUNDS

CROSS-REFERENCE TO RELATED APPLICATIONS

This application is a continuation of application Ser. No. 07/887,747, filed May 22, 1992, now abandoned, which is a continuation-in-part of U.S. Ser. No. 07/771,007 filed Oct. 2, 1991 now issued as U.S. Pat. No. 5,352,670, which, in turn, is a continuation-in-part of U.S. Ser. No. 07/714,161 filed Jun. 10, 1991, now abandoned; both of these applications are incorporated herein by reference in their entirety.

BACKGROUND OF THE INVENTION

FIELD OF THE INVENTION

The present invention is directed to novel sialyl Lewis$^a$ analogues, pharmaceutical compositions containing such analogues, methods for their preparation and methods for their use.

REFERENCES

The following references are cited in this application as superscript numbers at the relevant portion of the application:

1 Horowitz, the Glycoconjugates, Vols. I–V, Pigman, Editor, New York Academic Press (1977, 1978, 1982, 1983)
2 Ippolito et al., U.S. patent application Ser. No. 07/714,161, filed Jun. 10, 1991.
3 Sialic Acids in "Cell Biology Monographs" Schauer, Editor, Vol. 10 (1982)).
4 Schengrund et al., J. Biol. Chem., 264:13233–13237 (1989).
5 Paulson, "Interaction of Animal Viruses with Cell Surface Receptors" in "The Receptors", Conn, Ed., N.Y. Acad. Press, pp. 131–219 (1985).
6 Feizi, TIBS, 16:84–86 (1991).
7 Brandley et al., Cell, 63:861–863 (1990).
8 Hakomori, Adv. Cancer Res., 52:257–331 (1989)
9 Houghton et al., Symposium on Gangliosides and Cancer, pp. 233–237, VCH Publishers (1988)
10 Irie et al., Symposium on Gangliosides and Cancer, pp. 247–257, VCH Publishers (1988)
11 Howard, in "Towards Better Carbohydrate Vaccines"; Proceedings of a Meeting Organized by the World Health Organization, R. Bell, G. Torrigani, Editors, pp. 212–236, Wiley, Chichester (1987).
12 Henningsson et al., Cancer Immunol. Immunother., 25:231–241 (1987).
13 Fung et al., Cancer Res., 50:4308–4314 (1990).
14 Livingston et al., Proc. Natl. Acad. Sci. (USA), 84:2911–2915 (1987).
15 Naor et al., Prog. Allergy, 22:107–146 (1977).
16 Orshov et al., J. Exp. Med., 149:669–685 (1979).
17 Barsoum et al., Mol. Immunol., 18:495–550 (1981).
18 Jennings et al., U.S. Pat. No. 4,727,136 (1985).
19 Honda et al., J. Biochem., (Tokyo) 95:1323–1329 (1984).
20 Nakamura et al., J. Biochem., (Tokyo) 99:219–226 (1986).
21 Venot et al., "Methods for the Enzymatic Synthesis of Alpha-sialylated oligosaccharide Glycosides", U.S. patent application Ser. No. 07/771,007, filed Oct. 2, 1991.
22 Palcic et al., Carbohydr. Res., 190:1–11 (1989).
23 Ratcliffe et al., U.S. patent application Ser. No. 07/278,106, filed Nov. 30, 1988.
24 Weinstein et al., J. Biol. Chem., 257:13845–13853 (1982).
25 Rearick et al., J. Biol. Chem., 254:4444–4451 (1979).
26 Conradt et al., Japanese-German Symp. Berlin (1988) 104–105.
27 Prieels et al., J. Biol. Chem., 256:10456–10463 (1981).
28 Eppenberger-Castori et al., Glycoconj. J. 6:101–114 (1989).
29 Johnson et al., VIIIth Int. Symp. Glycoconjugates, Houston, 2:212–223 (1985).
30 Ritter et al., Immunobiology, 182:32–43 (1991).
31 Beyer et al., J. Biol. Chem., 254:12531–12541 (1979).
32 Paulson et al., Eur. J. Biochem., 140:523–539 (1984).
33 Reuter et al., Glycoconjugate J. 5:133–135 (1988).
34 Jiang et al., "Chemical Synthesis of GDP-Fucose", U.S. patent application Ser. No. 07/848,223 filed Mar. 9, 1992
35 Ratcliffe et al., U.S. Pat. No. 5,079,353
36 Higa et al., J. Biol. Chem., 260:8838–8849 (1985)
37 Brossmer et al., Biochem. Biophys. Acta., 96:1282–1289 (1980)
38 Gross et al., Eur. J. Biochem., 168:595–602 (1987)
39 Gross et al., Eur. J. Biochem., 177:583–589 (1988)
40 Christian et al., Carbohydr. Res., 194:49–61 (1987)
41 Conradt et al., FEBS Lett., 170:295–300 (1984)
42 Christian et al., Carbohydr. Res., 162:1–11 (1987)
43 Haverkamp et al., Hoppe-Seyler's Z. Physiol. Chem., 360:159–166 (1979)
44 Gross et al., Glycoconj. J., 4:145–156 (1987)
45 Hagedorn et al., XIIIth Carbohydr. Symp., Ithaca (1986) A4
46 Zbiral et al., Carbohydr. Res., 194:C15–C18 (1989)
47 Venot et al., "Methods for the Synthesis of Monofucosylated Oligosaccharide Terminating in Di-N-Acetyllactosaminyl Structures", U.S. patent application Ser. No. 07/771,259, filed Oct. 2, 1991
48 Ritter et al., Int. J. Cancer, 182:32–43 (1991).
49 Aplin et al., C.R.C. Crit. Rev. Biochem., pp. 259–306 (1981).
50 Dick et al., Glycoconjugates of Bacterial Carbohydrate Antigens in "Contributions to Microbiology and Immunology, Conjugate Vaccines", Crue et al. Eds. Basel, Karger, 10:48–114 (1989).
51 Lemieux et al., J. Amer. Chem. Soc., 97:4076–4083 (1975).
52 Pinto et al., Carbohydr. Chem., 124:313–318 (1983).
53 Bernstein et al., Carbohydr. Res., 78:C1–C3 (1980).
54 Lee et al., Carbohydr. Res. 37:193–201 (1974).
55 Gokhale et al., Can. J. Chem., 68:1063–1071 (1990)
56 Weinstein et al., J. Biol. Chem., 257:13835–13844 (1982)
57 Sticher et al., Biochem. J., 253:577–580 (1988)
58 Dean et al., Chromatogr., 165:301–319 (1979)
59 Mazid et al., "Process for the Separation and Purification of Sialyl Transferases", U.S. Pat. No. 5,059,535 (issued Oct. 22, 1991)
60 Palcic et al., Glycoconj. J., 5:49–63 (1988)
61 Bradford, Anal. Biochem., 72:248–254 (1976)
62 Paulson et al., J. Biol. Chem., 252:2363–2371 (1977)
63 Hanessian, Carbohydr. Res., 2:86–88 (1966)
64 Schmidt, et al., Liebigs Ann. Chem., 121–124 (1991)
65 Nunez, et al., Can. J. Chem., 59:2086–2095 (1981)
66 Veeneman, et al., Tetrahedron Lett., 32:6175–6178 (1991)
67 Kukowska-Latallo et al., Genes and Development, 4:1288–1303 (1990).
68 Dumas et al., Bioorg. Med. Letters, 1:425–428 (1991).
69 Greig et al., J. Chem. Soc., p. 879 (1961)
70 Piekarska-Bartowzewicz et al., Carbohydr. Res., 203:302–307 (1990)
71 Bodanszky et al., The Practice of Peptide Synthesis, Springer-Verlag (1984)

72 Inazu et al., Bull. Soc. Chim., Jap., 611:4467 (1988)
73 Bernotas et al., Biochem. J., 270:539–540 (1990)
74 Trumtez et al., Carbohydr. Res., 191:29–52 (1989)
75 Kovac et al., Carbohydr. Res., 169:23–34 (1987)
76 Petitou et al., Carbohydr. Res., 147221–236 (1986)
77 Belkhouya et al., Tetrahedron Letters, 3971–3980 (1991)
78 Wollenberg et al., U.S. Pat. No. 4,612,132
79 Petrakova et al., Can. J. Chemistry, 70:233–240 (1992)
80 Matsumoto et al., Anal. Biochem., 116:103–110 (1981)
81 Ekberg et al., Carbohydr. Res. 110:55–67 (1982)
82 Dahmen et al., Carbohydr. Res. 118:292–301 (1983)
83 Rana et al., Carbohydr. Res. 91:149–157 (1981)
84 Amvam-Zollo et al., Carbohydr. Res. 150:199–212 (1986)
85 Paulsen et al., Carbohydr. Res. 104:195–219 (1982)
86 Chernyak et al., Carbohydr. Res. 128:269–282 (1984)
87 Fernandez-Santana et al., J. Carbohydr. Chem. 8:531–537 (1989)
88 Lee et al., Carbohydr. Res., 37:193 et seq. (1974)

All publications and patent applications mentioned in this specification are indicative of the level of skill of those skilled in the art to which this invention pertains. All publications and patent applications are herein incorporated by reference in their entirety to the same extent as if each individual publication or patent application was specifically and individually indicated to be incorporated by reference in its entirety.

STATE OF THE ART

Carbohydrates and/or oligosaccharides are present on a variety of natural and pathological glycoconjugates[1]. Of particular interest are carbohydrates and oligosaccharides containing sialic acid residues particularly at the non-reducing sugar terminus[3]. Such sialic acid terminated carbohydrates and oligosaccharides are present in a number of products which have been implicated in a wide range of biological phenomena based, in part, on the concept of recognition signals carried by the carbohydrate structures and by their binding to specific ligands.

Specifically, such sialic acid terminated carbohydrates and oligosaccharides are believed to be receptors for the binding of toxins[4], pathogenic agents such as viruses[5], and are recognition sites for a variety of lectins, particularly those involved in cellular adhesion[6,7], etc. Sialylated and sialylated/fucosylated oligosaccharide structures relating to blood group determinants, including sialyl Lewis$^a$, have also been shown to possess in vivo immunomodulating and tolerogenic properties in mammals[2]. In this regard, the modified sialyl Lewis$^a$ compounds described herein also possess immunomodulating and tolerogenic properties.

Additionally, the presence of certain sialyl terminated oligosaccharides in tumor-related antigens is documented in the art[8] and, in general, the structures of the oligosaccharides present on such antigens have been modified in some way from normal oligosaccharides so as to lead to the expression of tumor related antigens[8]. The prospect of passive immunotherapy with monoclonal antibodies directed against some sialylated tumor-associated antigens, such as the gangliosides $GD_2$, $GD_3$, and $GM_2$, in patients with melanoma is being investigated[9,10]. However, most tumor-associated antigens are unable to lead to the production of tumor specific antibodies which would either inhibit or prevent the growth of such tumors. Without being limited to any theory, it is believed that this is due to the absence of real tumor specific antigens and that the structure of such antigens cross-reacts with that of similar structures expressed in a restricted number of normal tissues. In addition, carbohydrate antigens are generally not believed to lead to a T-cell mediated immune response that is expected to play a role in active immunity[11]. However, some recent studies indicate that, in some cases, tumor-associated carbohydrate antigens may stimulate anticancer T-cell immunity[12,13] or the production of cytotoxic antibodies[14].

In view of the general inability of carbohydrate tumor-related antigens to produce cytotoxic tumor specific antibodies, it has been proposed to chemically modify naturally occurring weak antigens so as to improve their antigenicity[15]. In this regard, methods for chemical modification of specific groups on sialylated carbohydrate tumor-related antigens have been reported.

Much of the focus of chemical modifications to non-or weakly-immunogenic naturally occurring antigens has been to derivatize the sialic acid residue of sialylated carbohydrate tumor-related antigens. Specifically, the art has reported that some structural modifications present on naturally occurring sialic acids renders the corresponding oligosaccharides immunogenic in selected hosts[16,17,18,19,20,30].

Recent work with artificial antigens indicates that while chemically modified sialosides (melanoma associated glycolipid antigens) are antigenic in humans, the antibodies generated in humans by these modified sialosides do not cross-react with the natural substance.[48] On the other hand, when injected into mice, chemically modified sialylated antigens produce antibodies which do cross-react with the natural substance. Accordingly, cross-reacting monoclonal or polyclonal antibodies generated in mice would serve as a basis for either a diagnostic assay for determining the presence and/or amount of the natural substance in a human host or as a basis for antibody therapy for a disease condition in which the natural substance is attack by the antibodies which can optionally be coupled to a therapeutic agent.

In regard to the above, Venot et al.[21] disclose a facile chemical/enzymatic synthesis of sialylated oligosaccharides containing modified sialyl groups at the non-reducing terminus of the oligosaccharide so as to produce a number of sialylated oligosaccharide structures having modifications to the sialic acid residue.

Notwithstanding the advantages of this synthetic method especially as they apply to sialyl Lewis$^a$ compounds modified in the sialyl unit, it would be further advantageous to modify both the galactose and/or the N-acetylglucosamine saccharide units in sialyl Lewis$^a$ so as to provide a variety of structures useful both in modulating an immune response and in preparing artificial antigens for the purpose of preparing antibodies thereto. From a practical point of view, it would be beneficial to prepare such analogues by a chemo/enzymatic approach where the sialic acid and fucose units are added to the modified βGal(1→3)βGlcNAc type I structure by appropriate sialyltransferases and fucosyltransferases respectively.

In the case of preparing sialyl Lewis$^a$ and analogues thereof, appropriate sialyltransferases include the known βGal(1→3/4)βGlcNAc α(2→3)sialyltransferase from rat liver[24] and the βGal(1→3)GalNAc α(2→3)sialyltransferase from porcine submaxillary glands[25] or liver[26] which cross reacts with the βGal(1→3)βGlcNAc structure to transfer sialic acid to the 3 position of the galactose to form an α(2→3) linkage. Appropriate fucosyltransferases include the known βGal(1→3/4)βGlcNAc α(1→3/4) fucosyltransferase which is readily obtained from human milk[22,27,28]. A recombinant form of βGal(1→3/4)βGlcNAc α(1→3/4)fucosyltransferase is also available[66,67].

In this regard, sialyl Lewis$^a$ structures have heretofore been prepared by a combined chemical/enzymatic approach which involves sequentially sialylating and fucosylating a βGal(1→3))βGlcNAc type I structure with appropriate glycosyltransferases[22,23]. Specifically, sialylation of the βGal(1→3)βGlcNAc type I structure involves contacting this structure with CMP-Neu5Ac in the presence of an appropriate sialyltransferase so as to place the Neu5Ac group at the 3 position of the galactose to form an α(2→3) linkage which results in the formation of αNeu5Ac(2→3)βGal(1→3)βGlcNAc. Fucosylation is then accomplished by contacting this compound with GDP-fucose in the presence of an appropriate fucosyltransferase so as to place a fucose substituent at the 4 position of the GlcNAc to form an α(1→4) linkage which results in the formation of αNeu5Ac(2→3)βGal(1→3) [αFuc(1→4)]βGlcNAc (i.e., sialyl Lewis$^a$).

In regard to the above, the use of sialyltransferases and fucosyltransferases provides for the most facile method for the synthesis of sialyl Lewis$^a$ because, under these conditions, sialylation and fucosylation do not require protection/deprotection of reactive moieties at other sites of the oligosaccharide structure as is common in chemical synthesis. Moreover, sialyltransferases readily form the α(2→3) linkage which is otherwise difficult to form in high yield with anomeric specificity.

The art recognizes that certain modifications can be tolerated by the βGal(1→3/4)βGlcNAc α(1→3/4) fucosyltransferase on the 2 and 3 positions of the galactose structures of βGal(1→3)βGlcNAc[22,29] but that the presence of a Neu5Ac or deoxy group at the 6-position of the galactose cannot be tolerated by this enzyme. However, it is not known what modifications on the N-acetylglucosamine saccharide unit of βGal(1→3)βGlcNAc disaccharide or the αNeu5Ac(2→3)βGal(1→3)βGlcNAc trisaccharide would be tolerated by this fucosyltransferase.

Similarly, while the art has heretofore disclosed that βGal(1→3/4)βGlcNAc α(2→3)sialyltransferase will not transfer Neu5Ac to a 3 position of the galactose unit of βGal(1→3) [αFuc(1→4)]βGlcNAc structure[31] but will transfer Neu5Ac to the α(2→3) position of the galactose unit of βGal(1→3) [αFuc(1→6)]βGlcNAc- structure[32], it is not known what other modifications, if any, on the βGal(1→3)βGlcNAc type I structure would be tolerated by βGal(1→3/4)βGlcNAc α(2→3)sialyltransferase or the βGal(1→3)GalNAc α(2→3)sialyltransferase.

This uncertainty made it difficult to provide any rationale method for modifying the galactose and/or N-acetylglucosamine units of the βGal(1→3)βGlcNAc type I structure with the expectation of sequentially sialylating and fucosylating this structure by using the βGal(1→3/4)βGlcNAc α(2→3)sialyltransferase or the βGal(1→3)GalNAc α(2→3)sialyltransferase and then using the βGal(1→3/4)βGlcNAc α(1→3/4)fucosyltransferase or any other available and acceptable transferase.

In view of the above, it would be particularly beneficial to develop modified sialyl Lewis$^a$ structures which would possess immunomodulating and tolerogenic properties as well as which could be used as antigenic determinants on artificial antigens so as to prepare monoclonal and polyclonal antibodies. It would be further beneficial if these modified sialyl Lewis$^a$ structures could be readily prepared by sequentially sialylating and fucosylating a modified βGal(1→3)βGlcNAc structure with an appropriate sialyltransferase and an appropriate fucosyltransferase.

SUMMARY OF THE INVENTION

The present invention is directed in part to the discovery that the modified sialyl Lewis$^a$ compounds described herein are useful in both modulating a cell-mediated immune response to an antigen in vivo while providing tolerance to later challenges from that antigen as well as in preparing artificial antigens to produce antibodies directed to these structures. In this regard, the monoclonal or polyclonal antibodies raised against these artificial antigens (especially in mice) are useful in diagnostic assays for determining the presence of sialyl Lewis$^a$ structures in human hosts. Additionally, it is contemplated that these antibodies would be useful in antibody therapy for a disease condition wherein the antibody would attach to sialyl Lewis$^a$ type antigenic structures on diseased particles (e.g., cancer cells).

The present invention is directed to the further discovery that the modifications made to the galactose and/or N-acetylglucosamine units of sialyl Lewis$^a$ are compatible with specified sialyl- and fucosyltransferases so that the sialyl and fucosyl residues on these compounds are readily prepared by sequential enzymatic methods.

Specifically, it has now been discovered that the βGal(1→3/4)βGlcNAc α(2→3)sialyltransferase and the βGal(1→3)GalNAc α(2→3)sialyltransferase can accept extensive modifications to the 2 and 6 positions of the N-acetylglucosamine unit as well as some modification at the 2 position of the galactose unit of βGal(1→3)βGlcNAc type I structures and still readily transfer sialic acid to the 3 position of the galactose to form an α(2→3) linkage on the galactose saccharide. Similarly, it has now been discovered that the βGal(1→3/4)βGlcNAc α(1→3/4)fucosyltransferase can accept extensive modifications to the 6 position and some modification to the 2 position of the N-acetylglucosamine unit as well as non-oxygen containing modifications at the 2-position of the galactose saccharide of the βGal(1→3)βGlcNAc type I structure and still readily transfer L-fucose to form an α(1→4) linked fucose residue on the N-acetylglucosamine structure.

In view of these discoveries, we concluded that the overlap of modifications permitted by the βGal(1→3/4)βGlcNAc α(2→3)sialyl- and the βGal(1→3/4)βGlcNAc α(1→3/4) fucosyl-transferases allowed for modifications at the 2 and 6 positions of the N-acetylglucosamine and the 2 position of the galactose units of βGal(1→3)βGlcNAc type I structures and still permit sequential sialylation and fucosylation by the respective transferases.

Accordingly, in one of its composition aspects, this invention is directed compounds which are suitable for use in modulating a cell-mediated immune response to an antigen in a mammal which compounds are represented by Formula I:

$$\text{HO} \underset{R_4O}{\overset{OH}{\diagup}} \!\!\!\! \diagdown_O \diagup \underset{R_3}{\diagdown} \diagup \underset{R_2}{\diagdown}_O \diagup \overset{R_1}{\diagup} \!\!\!\! \diagdown_O \diagup \diagdown Y{-}R \qquad \text{I}$$

where R is selected from the group consisting of hydrogen, a saccharide, an oligosaccharide, or an aglycon having at least 1 carbon atom;

$R_1$ is selected from the group consisting of hydrogen, $-NH_2$, $-N_3$, $-NHSO_3H$, $-NR_8C(O)R_6$, $-N{=}C(R_7)_2$, $-NHCH(R_7)_2$, $-N(R_8)_2$, $-O(C(O))_pR_9$, $-SR_8$, fluoro, chloro, bromo, and sulfate, wherein $R_6$ is selected from the group consisting of hydrogen,
alkyl of from 1 to 4 carbon atoms optionally substituted with 1 or more substituents selected from the group consisting of hydroxy, chloro, bromo, alkoxy of from 1 to 4 carbon atoms, phenyl, and phenyl substituted with 1 to 3 substituents selected from the group consisting of hydroxy, alkyl of from 1 to 4 carbon atoms, alkoxy of from 1 to 4 carbon atoms, chloro, bromo, and sulfate, an amino acid or polypeptidyl residue, —$OR_{10}$ wherein $R_{10}$ is alkyl of from 1 to 4 carbon atoms, or alkyl of from 2 to 4 carbon atoms substituted with a hydroxyl group, and —$NR_{11}R_{12}$ wherein $R_{11}$ and $R_{12}$ are independently selected from the group consisting of hydrogen and alkyl of from 1 to 4 carbon atoms, each $R_7$ is independently selected from the group consisting of hydrogen and alkyl of from 1 to 4 carbon atoms, $R_8$ is independently selected from the group consisting of hydrogen and alkyl of from 1 to 4 carbon atoms, $R_9$ is selected from the group consisting of hydrogen, alkyl of from 1 to 4 carbon atoms optionally substituted with 1 or more substituents selected from the group consisting of hydroxy, chloro, bromo, alkoxy of from 1 to 4 carbon atoms, phenyl, and phenyl substituted with 1 to 3 substituents selected from the group consisting of hydroxy, alkyl of from 1 to 4 carbon atoms, alkoxy of from 1 to 4 carbon atoms, chloro, bromo, and sulfate, and p is an integer equal to 0 or 1;

$R_2$ is selected from the group consisting of hydrogen, —$N_3$, —$NH_2$, —$NHSO_3H$, —$NR_{15}C(O)R_{13}$, —$N=C(R_{14})_2$, —$NHCH(R_{14})_2$, —$N(R_{15})_2$, —$O(C(O))_qR_{16}$, fluoro, chloro, bromo and sulfate, wherein $R_{13}$ is selected from the group consisting of hydrogen, alkyl of from 1 to 4 carbon atoms optionally substituted with 1 or more substituents selected from the group consisting of hydroxy, chloro, bromo, and alkoxy of from 1 to 4 carbon atoms, an amino acid or polypeptidyl residue, —$OR_{17}$ wherein $R_{17}$ is alkyl of from 1 to 4 carbon atoms, or alkyl of from 2 to 4 carbon atoms substituted with a hydroxyl group, and —$NR_{18}R_{19}$ wherein $R_{18}$ and $R_{19}$ are independently selected from the group consisting of hydrogen and alkyl of from 1 to 4 carbon atoms, each $R_{14}$ is independently selected from the group consisting of hydrogen and alkyl of from 1 to 4 carbon atoms, each $R_{15}$ is independently selected from the group consisting of hydrogen and alkyl of from 1 to 4 carbon atoms, $R_{16}$ is selected from the group consisting of hydrogen, alkyl of from 1 to 4 carbon atoms optionally substituted with from 1 to 4 carbon atoms substituted with 1 or more substituents selected from the group consisting of hydroxy, chloro, bromo, and alkoxy of from 1 to 4 carbon atoms, and q is an integer equal to 0 or 1;

$R_3$ is selected from the group consisting of hydrogen, fluoro, and hydroxy;

$R_4$ is sialyl;

$R_5$ is L-fucosyl;

Y is selected from the group consisting of O, S, —NH—, and a bond; and pharmaceutically acceptable salts thereof and with the proviso that when $R_1$ is hydroxyl and $R_2$ is —$NHC(O)CH_3$ then $R_3$ is not hydroxyl.

Preferably, in Formula I, $R_1$ is hydroxyl, alkoxy of from 1 to 4 carbon atoms, chloro, bromo, or fluoro. $R_2$ is preferably —$NH_2$, —$NHC(O)R_{13}$, or —$N_3$. $R_3$ is preferably hydroxyl.

The compounds of Formula I are particularly useful in modulating a cell-mediated immune inflammatory response.

In another of its composition aspects, the present invention is directed to a pharmaceutical composition suitable for administration to a mammal (e.g., human) which comprises a pharmaceutically inert carrier and an effective amount of the compound of Formula I to modulate a cell-mediated immune response in said mammal.

When R is an aglycon capable of being linked to a carrier, then the compounds of Formula I are also useful in preparing artificial antigens. Accordingly, in still another of its composition aspects, the present invention is directed to artificial antigens prepared from a compounds of Formula I which contains an aglycon moiety capable of being linked to an antigenic carrier.

In still yet another of its composition aspects, the present invention is directed to novel intermediates useful in the preparation of a compound of Formula I.

In one of its method aspects, the present invention is directed to a method for modulating a cell-mediated immune response in a mammal which method comprises administering to said mammal an amount of a compound of Formula I effective in modulating said immune response.

In another of its method aspects, the present invention is directed to a method for preparing a compound of Formula I which comprises (a) selecting a compound of Formula II

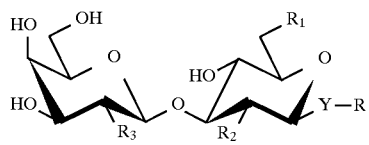

wherein R, $R_1$, $R_2$, $R_3$, and Y are as defined above;

(b) sialylating said compound at the 3 position of the galactose moiety with a sialyltransferase selected from the group consisting of βGal(1→3/4)βGlcNAc α(2→3)sialyltransferase and βGal(1→3)GalNAc α(2→3)sialyltransferase so as to place a sialyl residue at the 3 position of the galactose unit in an α(2→3) linkage; and (c) fucosylating the compound produced in step (b) at the 4 position of the N-acetylglucosamine moiety with βGal(1→3/4)βGlcNAc α(1→3/4)fucosyltransferase so as to place a fucosyl residue at the 4 position of the N-acetylglucosamine unit in an α(1→4) linkage.

DETAILED DESCRIPTION OF THE PREFERRED EMBODIMENTS

Figure 1:
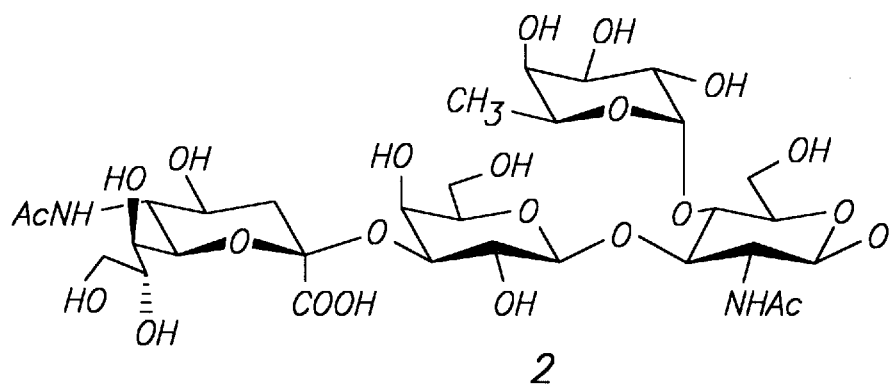
FIG. 1 illustrates the structures of sialyl Lewis$^a$ (compound 2) of analogues of sialyl Lewis$^a$ having a substituent at the 2 position of the N-acetylglucosamine unit (compounds 8b–d) and intermediates used in preparing the analogues of sialyl Lewis$^a$ (compounds 7b–d).
Figure 1:
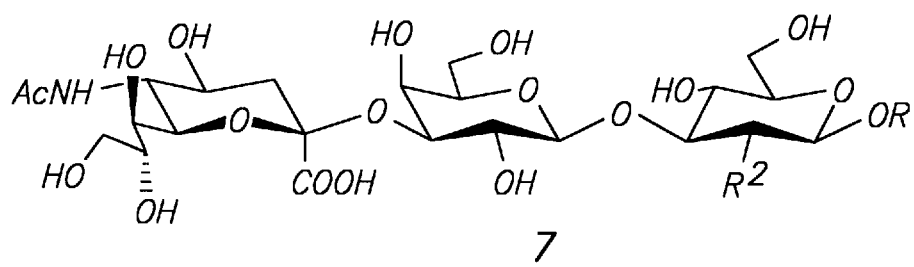
Figure 1:
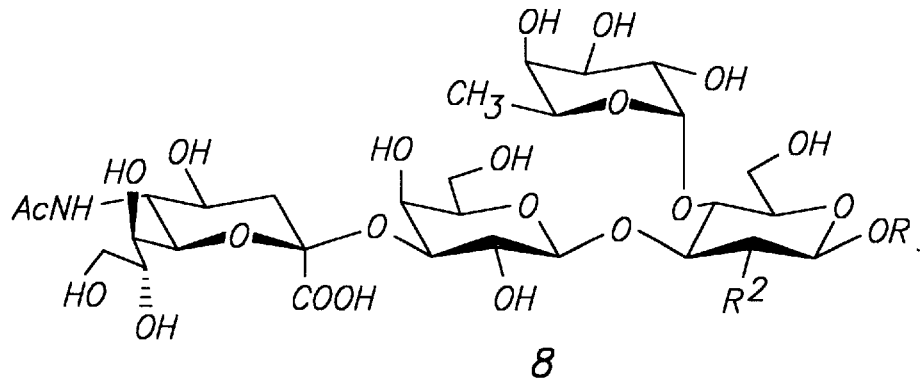

As noted above, the present invention is directed, in part, to the discovery of novel sialyl Lewis$^a$ analogues which, in mammals, are useful for in vivo modulation of a cell mediated immune response. Additionally, when an appropriate aglycon is employed, these sialyl Lewis$^a$ analogues can also be used to prepare artificial antigens for the generation of monoclonal or polyclonal antibodies to sialyl Lewis$^a$.

Additionally, the present invention is directed, in part, to novel methods for the synthesis of sialyl Lewis$^a$ analogues.

However, prior to discussing this invention in further detail, the following terms will first be defined.

Definitions

As used herein, the following terms have the definitions given below:

The term "sialyl Lewis$^a$" (sometimes referred to "SLe$^a$") refers to the tetrasaccharide having the following structure:

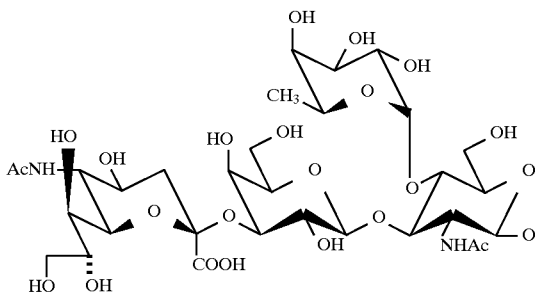

Because of its relationship to blood group determinants, the core βGal(1→3)βGlcNAc structure of sialyl Lewis$^a$ is often referred as a "type I structure".

The term "oligosaccharide" refers to a carbohydrate structure having from 2 to about 10 saccharide units. The particular saccharide units employed are not critical and include, by way of example, all natural and synthetic derivatives of glucose, galactose, N-acetylglucosamine, N-acetylgalactosamine, fucose, sialic acid, 3-deoxy-D,L-octulosonic acid, and the like.

In addition to being in their pyranose form, all saccharide units described herein are in their D form except for fucose which is in its L form.

The term "sialic acid" or "sialyl" means all naturally occurring structures of sialic acid and analogues of sialic acid which, as their CMP-derivatives, are compatible with βGal(1→3/4)βGlcNAc α(2→3)sialyltransferase and/or βGal(1→3)GalNAc α(2→3)sialyltransferase. In this regard, any sialic acid which, as its CMP-derivative, is recognized by either or both of these sialyltransferases so as to bind to the enzyme(s) and is then available for transfer to the compound of Formula II above is said to be compatible with the sialyltransferase.

Naturally occurring structures of sialic acid include, by way of example, 5-acetamido-3,5-dideoxy-D-glycero-D-galacto-nonulopyranosylonic acid ("Neu5Ac"), N-glycoyl neuraminic acid (Neu5Gc) and 9-O-acetyl neuraminic acid (Neu5, 9Ac$_2$). A complete list of naturally occurring sialic acids known to date are provided by Schauer[3].

Analogues of sialic acid refers to analogues of naturally occurring structures of sialic acid including those wherein the sialic acid unit has been chemically modified so as to introduce and/or remove one or more functionalities from such structures. For example, such modification can result in the removal of an —OH functionality, the introduction of an amine functionality, the introduction of a halo functionality, and the like.

Certain analogues of sialic acid are known in the art and include, by way of example, 9-azido-Neu5Ac, 9-amino-Neu5Ac, 9-deoxy-Neu5Ac, 9-fluoro-Neu5Ac, 9-bromo-Neu5Ac, 7-deoxy-Neu5Ac, 7-epi-Neu5Ac, 7,8-bis-epi-Neu5Ac, 4-O-methyl-Neu5Ac, 4-N-acetyl-Neu5Ac, 4,7-dideoxy-Neu5Ac, 4-oxo-Neu5Ac, as well as the 6-thio analogues of Neu5Ac. The nomenclature employed herein in describing analogues of sialic acid is as set forth by Reuter et al.[33]

CMP-nucleotide derivative of sialic acid refers to the cytidine-5-monophosphate derivative of a naturally occurring sialic acid or an analogue thereof. In the case where the sialic acid is Neu5Ac, the CMP derivative has the formula:

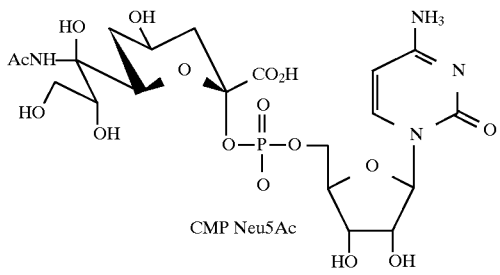

CMP Neu5Ac

The term "fucose" or "fucosyl" refers to L-fucose and analogues thereof which, as their GDP-derivatives, are compatible with βGal(1→3/4)βGlcNAc α(1→3/4) fucosyltransferase. As noted below, this fucosyltransferase is readily isolated from human milk. Additionally, it is contemplated that these fucose or fucosyl compounds will also be compatible with other fucosyltransferases of appropriate specificity such as cloned fucosyltransferases[67,68].

In regard to the above, any fucose compound which, as its GDP-derivative, is recognized by the βGal(1→3/4) βGlcNAc α(1→3/4)fucosyltransferase so as to bind to the enzyme and is then available for transfer to the compound of Formula III:

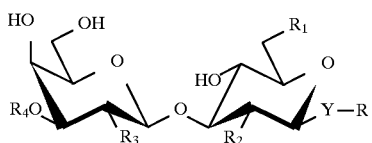

where R$_4$, is sialyl or hydrogen, is said to be compatible with this fucosyltransferase.

Analogues of fucose refer to naturally occurring and synthetic analogues of fucose including those where the fucose unit has been chemically modified so as to introduce and/or remove one or more functionalities from this structure. For example, such modification can result in the removal of an —OH functionality, the introduction of an amine functionality, the introduction of a halo functionality, and the like.

Certain compatible analogues of fucose are known in the art and include, by way of example, 3-deoxy-fucose, arabinose, and the like.[55]

The GDP-derivative of fucose refers to guanosine 5'(β-L-fucopyranosyl)diphosphate and any and all compatible salts thereof which has the formula:

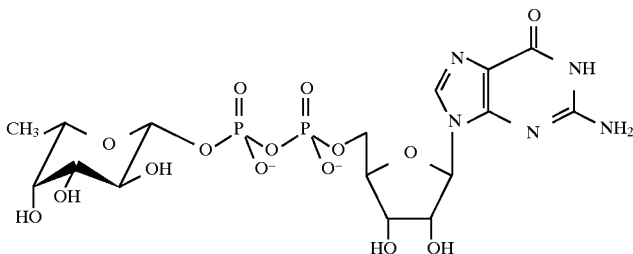

Methods for preparing GDP-fucose are known in the art. However, GDP-fucose is preferably prepared by the method described by Jiang et al.[34] in U.S. patent application Ser. No. 07/848,223 which is incorporated herein by reference in its entirety.

The term "compatible salts" as it is used in relation to guanosine 5'-(β-L-fucopyranosyl)diphosphate refers to those salts of guanosine 5'-(β-L-fucopyranosyl)diphosphate which readily form counter ions (i.e., cations) and which are compatible with the intended reactions and/or purifications. Suitable compatible salts include those prepared from counter ions such as sodium, potassium, lithium, calcium, magnesium, ammonium, mono-, di-, tri- or tetra-alkylammonium, iron, zinc, and the like.

The term "amino acid or polypeptidyl residue" refers to product obtained by reacting an appropriate form of an amino acid or a polypeptide with an oligosaccharide glycoside of Formula I or an intermediate used to prepare the compounds of FIG. I and which has an amine functionality (—NH$_2$) at the 2 or 6 positions of the GlcNAc unit under conditions where the amine reacts with a carboxyl group or an activated carboxyl group on the amino acid or peptide to form an amide bond. The particular amino acid or polypeptide employed is not critical. However, in a preferred embodiment, the polypeptide contains from about 2 to about 5 amino acids and even more preferably from about 2 to 3 amino acids.

The term "pharmaceutically acceptable salts" includes the pharmaceutically acceptable addition salts of the compounds of Formula I derived from a variety of organic and inorganic counter salts well known in the art and include, by way of example only, sodium, potassium, calcium, magnesium, ammonium, tetralkylammonium, and the like.

The term "removable blocking group" refers to any group which when bound to one or more hydroxyl groups of the galactose, N-acetylglucosamine, the sialic acid (including the hydroxyl group of the carboxylic acid moiety) and/or the fucose units of sialyl Lewis$^a$ moieties prevents reactions from occurring at these hydroxyl groups and which protecting group can be removed by conventional chemical or enzymatic steps to reestablish the hydroxyl group. The particular removable blocking group employed is not critical and preferred removable hydroxyl blocking groups include conventional substituents such as benzyl, acetyl, chloroacetyl, benzylidine, t-butyldiphenylsilyl and any other group that can be introduced either enzymatically or chemically onto a hydroxyl functionality and later selectively removed either by enzymatic or chemical methods in mild conditions compatible with the nature of the product. One such additional contemplated blocking group is a α-galactose which can be removed enzymatically with an α-galactosidase.

The term "aglycon of at least one carbon atom" refers to non-saccharide containing residues having at least one carbon atom. Preferably, the aglycon is selected from the group consisting of —(A)—Z wherein A represents a bond, an alkylene group of from 2 to 10 carbon atoms, and a moiety of the form —(CH$_2$—CR$_{20}$G)$_n$—wherein n is an integer equal to 1 to 5; R$_{20}$ is selected from the group consisting of hydrogen, methyl, or ethyl; and G is selected from the group consisting of hydrogen, halogen, oxygen, sulphur, nitrogen, phenyl and phenyl substituted with 1 to 3 substituents selected from the group consisting of amine, hydroxyl, halo, alkyl of from 1 to 4 carbon atoms and alkoxy of from 1 to 4 carbon atoms; and Z is selected from the group consisting of hydrogen, methyl, phenyl, nitro-phenyl and, when G is not oxygen, sulphur or nitrogen and A is not a bond, then Z is also selected from the group consisting of —OH, —SH, —NH$_2$, —NHR$_{21}$, —N(R$_{21}$)$_2$, —C(O)OH, —C(O)OR$_{21}$, —C(O)NH—NH$_2$, —C(O)NH$_2$, —C(O)NHR$_{21}$, —C(O)N(R$_{21}$)$_2$, and —OR$_{22}$ wherein each R$_{21}$ is independently alkyl of from 1 to 4 carbon atoms and R$_{22}$ is an alkenyl group of from 3 to 10 carbon atoms.

When the alpha-sialylated oligosaccharide glycoside is used for preparing an artificial conjugate, then the aglycon, R, is then R$_{23}$, which is a group capable of being linked to a carrier. Preferably, R$_{23}$ is selected from the group consisting of —(A)—Z' wherein A is selected from the group consisting of an alkylene group of from 2 to 10 carbon atoms, and a moiety of the form —(CH$_2$—CR$_{24}$G)$_n$— wherein n is an integer equal to 1 to 5; R$_{24}$ is selected from the group consisting of hydrogen, methyl, or ethyl; and G is selected from the group consisting of hydrogen, oxygen, sulphur, nitrogen, phenyl and phenyl substituted with 1 to 3 substituents selected from the group consisting of amine, hydroxyl, halo, alkyl of from 1 to 4 carbon atoms and alkoxy of from 1 to 4 carbon atoms; and Z' is selected from the group consisting of hydrogen and, when G is not oxygen, sulphur or nitrogen, then Z' is also selected from the group consisting of —OH, —SH, —NH$_2$, —NHR$_{25}$, —C(O)OH, —C(O)OR$_{25}$, —C(O)NHNH$_2$, and —OR$_{26}$ wherein each R$_{25}$ is independently alkyl of from 1 to 4 carbon atoms and R$_{26}$ is an alkenyl group of from 3 to 10 carbon atoms with the proviso that when A is a bond, Z' s not hydrogen. In such cases, the —(A)—Z' group defines a group capable of being linked to a carrier or is capable of being derivatized to a group which is capable of being linked to a carrier. The choice of an appropriate carrier may be useful in enhancing immunogenic properties.

Numerous aglycons are known in the art. For example, a linking arm comprising a para-nitrophenyl group (i.e., —YR=—OC$_6$H$_4$pNO$_2$) has been disclosed by Ekborg et al.[81] At the appropriate time during synthesis, the nitro group is reduced to an amino group which can be protected as N-trifluoroacetamido. Prior to coupling to a support, the trifluoroacetamido group is removed thereby unmasking the amino group.

A linking arm containing sulfur is disclosed by Dahmen et al.[82]. Specifically, the linking arm is derived from a 2-bromoethyl group which, in a substitution reaction with thio-nucleophiles, has been shown to lead to linking arms possessing a variety of terminal functional groups such as —OCH$_2$CH$_2$SCH$_2$SCO$_2$CO$_3$ and —OCH$_2$CH$_2$SC$_6$H$_4$—pNH$_2$.

Rana et al.[83] discloses a 6-trifluoroacetamido)-hexyl linking arm (—O—(CH$_2$)$_6$—NHCOCF$_3$) in which the trifluoroacetamido protecting group can be removed unmasking the primary amino group used for coupling.

Other exemplification of known linking arms include the 7-methoxycarbonyl-3,6,dioxaheptyl linking arm[84] (—OCH$_2$—CH$_2$)$_2$OCH$_2$CO$_2$CH$_3$; the 2-(4-methoxycarbonylbutancarboxamido)ethyl[85] (—OCH$_2$CH$_2$NHC(O) (CH$_2$)$_4$CO$_2$CO$_3$; the allyl linking arm[86] (OCH$_2$CH=CH$_2$) which, by radical co-polymerization with an appropriate monomer,leads to co-polymers; other allyl linking arms[87] [—O(CH$_2$CH$_2$O)$_2$CH$_2$CH=CH$_2$]. Additionally, allyl linking arms can be derivatized in the presence of 2-aminoethanethiol[88] to provide for a linking arm —OCH$_2$CH$_2$CH$_2$SCH$_2$CH$_2$NH$_2$.

Additionally, as shown by Ratcliffe et al.[23], R group can be an additional saccharide or an oligosaccharide containing a linking arm at the reducing sugar terminus.

Preferably, the aglycon moiety is a hydrophobic group and most preferably, the aglycon moiety is a hydrophobic group selected from the group consisting of —(CH$_2$)$_8$COOCH$_3$, —(CH$_2$)$_5$OCH$_2$CH=CH$_2$ and —(CH$_2$)$_8$CH$_2$OH. In particular, the use of a hydrophobic group and most especially, a —(CH$_2$)$_8$COOCH$_3$, or —(CH$_2$)$_5$OCH$_2$CH=CH$_2$ or —(CH$_2$)$_8$CH$_2$OH group may provide for some enhancement of the acceptor properties for transfer of sialic acid by this sialyltransferase.

The carrier is a low or high molecular weight, non-immunogenic or antigenic carrier including the linking to a fluorescent label, a radioactive label, biotin, or a photolabile linking arm or a moiety to be targeted. Preferably, the carrier is an antigenic carrier and accordingly, the artificial conjugate is an artificial antigen. In some cases it may be advantageous to employ a non-immunogenic carrier.

On the other hand, the carrier can be a low molecular weight carrier such as ethylene diamine, hexamethylene diamine, tris(2-aminoethyl)amine, L lysilysine, poly-L-lysine, and polymers of various molecular weights.

The term "antigenic carrier" refers to a carrier containing one or more functional groups which permit linking of an oligosaccharide glycoside of Formula I (where R=R$_{23}$) to the carrier and which produces an antigenic response when injected into animals to which the particular carrier is not endogenous. Such carriers can be proteins [e.g., bovine serum albumin (BSA), human serum albumin (HSA), diphtheria or tetanus toxoid, S-layers, and the like] and are sometimes referred to herein by the abbreviation "Ag".

The particular antigenic carrier selected for use in preparing an artificial antigen is not critical provided it contains or can be derivatized to contain one or more functional groups which permit linking to the carrier of such an oligosaccharide glycoside. Suitable functional groups include, by way of example, carboxylic acid groups, amines groups (including primary and secondary amines), hydroxyl groups, thio groups, and the like. Such functional groups are commonly found on antigenic carriers (e.g., proteins contain numerous such functionality) and/or can be introduced onto such carriers via art recognized methods.

Coupling of one or more of the oligosaccharide glycosides of Formula I to the antigenic carrier results in a product which is described herein as an "artificial antigen" because when injected into an animal, this antigen will possess one or more non-naturally occurring oligosaccharide glycoside determinants. The artificial antigens so produced are preferably represented by the formula:

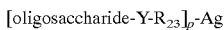

[oligosaccharide-Y-R$_{23}$]$_p$-Ag wherein oligosaccharide-Y represents the compound of formula I above (where R is R$_{23}$), R$_{23}$ and Ag are as defined above, and p is an integer equal to at least 1. In this embodiment, the artificial antigen, Ag, is linked to the oligosaccharide glycoside through a functional group on the antigen which couples to a complimentary functional group on the aglycon group, i.e., the R$_{23}$ group.

The term "antibody" refers to an immunoglobulin, or derivative thereof, having an area on the surface or in a cavity which specifically binds to and is thereby defined as complementary with a particular spatial and polar organization of another molecule. The antibody can be monoclonal or polyclonal and can be prepared by techniques that are well known in the art, such as, for example, immunization of a host and collection of sera or hybrid cell line technology.

In this regard, the artificial antigens described above are useful in generating antibodies which recognize and are complementary to the antigenic determinants, including the sialyl Lewis$^a$ determinants, on the antigen as well as which cross-reacts with the natural substance.

The term "natural substance" refers to a naturally occurring material associated with a defined disease condition (e.g., a tumor-associated carbohydrate antigen) which material contains one or more sialyl Lewis$^a$ moieties and which material is either non-immunogenic or weakly immunogenic in the diseased mammal.

B. Methodology

As indicated above, this invention is directed, in part, to novel analogues of sialyl Lewis$^a$ which are useful in both modulating a cell-mediated immune response to an antigen as well as in providing for artificial antigens for the creation of antibodies. These novel analogues of sialyl Lewis$^a$ can be prepared by a variety of synthetic pathways as set forth in the figures.

In a preferred embodiment, the analogues of sialyl Lewis$^a$, as set forth in Formula I, are prepared by first synthesizing the βGal(1→3)βGlcNAc-OR backbone derivatized at the 2 and/or 6 positions of the N-acetylglucosamine unit and/or at the 2 position of the galactose unit. This backbone is then sequentially sialylated and fucosylated using the βGal(1→3/4)βGlcNAc α(2→3)sialyltransferase or the βGal(1→3)GalNAc α(2→3)sialyltransferase and the βGal(1→3/4)βGlcNAc α(1→3/4)fucosyltransferase.

The use of such sialyltransferases and fucosyltransferase provides for the facile synthesis of analogues of sialyl Lewis$^a$ including those having modification on either the sialyl and/or fucosyl groups. For example, use of these transferases permits the transfer of Neu5Ac or analogues of Neu5Ac to the backbone structure as well as the transfer of fucose and analogues thereof to this backbone structure.

However, there are alternative methods for preparing these compounds including methods which rely on total chemical synthesis as well as on only partial enzymatic synthesis. General schemes, as set forth in FIGS. 2–9, for the production of analogues of sialyl Lewis$^a$ or intermediates therefor are now discussed in more detail.

In those cases where the sialyl Lewis$^a$ analogues are to be used to prepare artificial antigens, these analogues are coupled to antigenic carriers and then injected into an appropriate animal to generate antibodies.

Figure 2:
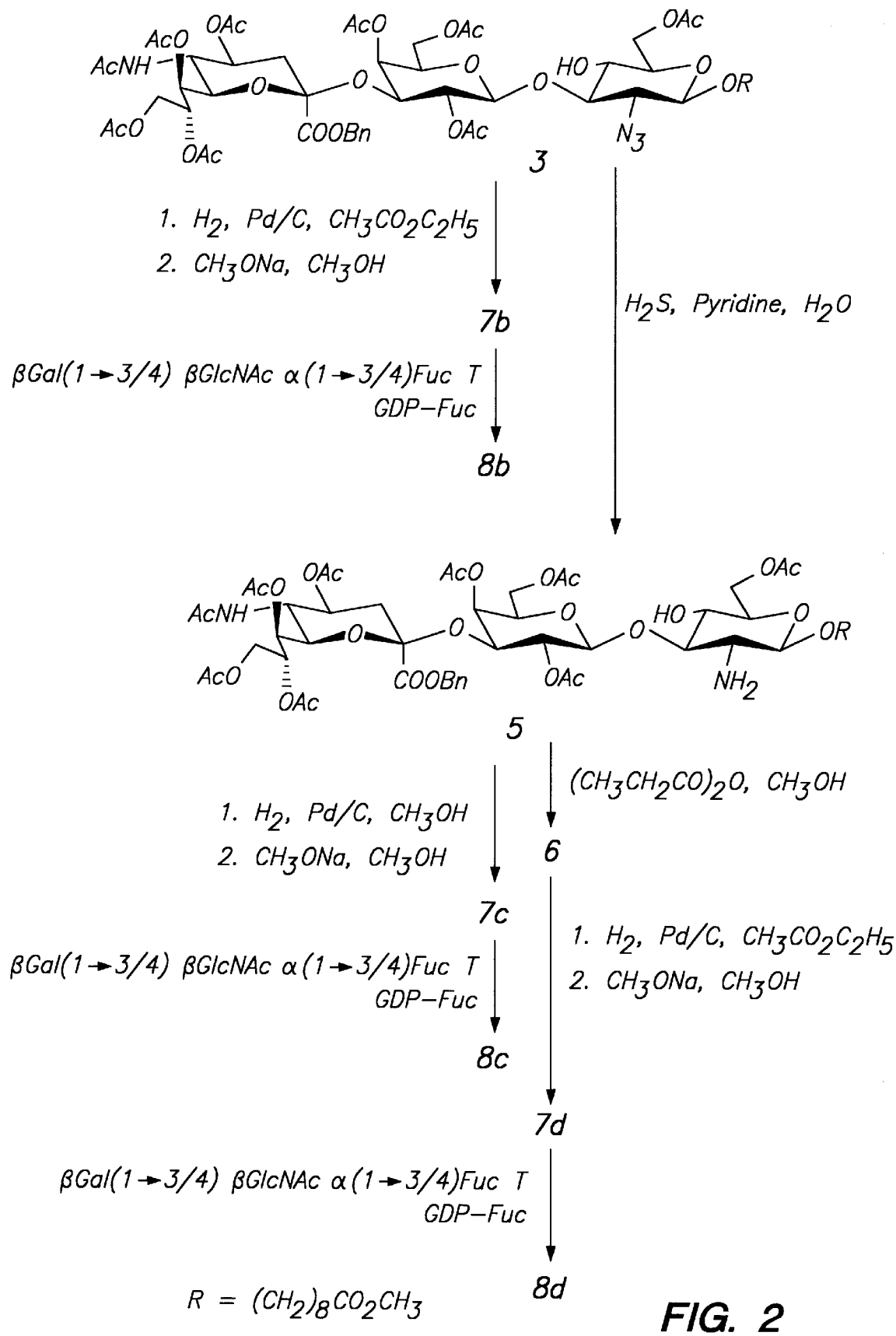
FIG. 2 illustrates a general reaction scheme for the chemo-enzymatic synthesis of the analogues of sialyl Lewis$^a$ (compound 8b–d) set forth in FIG. 1 wherein Ac represent acetyl, Bn represents benzyl, and R represents —$(CH_2)_8CO_2CH_3$.

B1. Chemo-Enzymatic Synthesis of Sialyl Lewis$^a$ Tetrasaccharides Modified at the C-2 or C-6 Positions of the N-Acetylglucosamine Trisaccharide 3 set forth in FIG. 2 is a known compound and is disclosed by Ratcliffe et al[35]. This compound is then derivatized by conventional steps well known in the art to provide for a trisaccharides 7b, 7c, and 7d described in FIG. 1.

Specifically, hydrogenation ($H_2$) of the benzyl ester (—COOBn) of trisaccharide 3 at atmospheric pressure in ethyl acetate ($CH_3CO_2C_2H_5$) in the presence of 5% palladium on carbon (Pd/C), followed by de-O-acetylation with sodium methoxide in methanol ($CH_3ONa$, $CH_3OH$) provided trisaccharide 7b. The use of ethyl acetate as solvent is recommended in the first step in order to leave the 2-azido group untouched. Only a very small amount of impurity is formed in this step which can be separated by conventional separation techniques (e.g., chromatography).

Alternatively, reduction of the 2-azido group of tetrasaccharide 3 by hydrogen sulfide ($H_2S$) in a mixture of pyridine, water and triethylamine provided the 2-amino trisaccharide 5. Reduction of the benzyl ester (—COOBn) followed by de-O-acetylation (as described above) lead to trisaccharide 7c.

Trisaccharide 7d is prepared by first conducting N-propionylation of trisaccharide 5 using propionic anhydride [($CH_3CH_2CO)_2O$] in methanol ($CH_3OH$) to provide for trisaccharide 6. Trisaccharide 6 was accompanied by a small amount of the corresponding 4-O-propionylated material which can be separated by conventional separation techniques (e.g., chromatography). Removal of the acetyl and benzyl protecting groups, as indicated above, provided the trisaccharide 7d.

Trisaccharide 5 can also be derivatized by conventional methods to provide for —H, —NHC(O)$R_{13}$, —NHSO$_3$H, —N=C($R_{14}$)$_2$, —NHCH($R_{14}$)$_2$ —N($R_{15}$)$_2$, and an amino acid or polypeptidyl residue derivatives by conventional methods. For example, the —NH$_2$ group can be reacted, using conventional techniques, with:

a carboxylic acid, anhydride or chloride to provide for amides (e.g., as per the formation of the propionamide of trisaccharide 7d). Alternatively, the desired acid can be activated, as reported by Inazu et al[72] and then reacted with the amino group. The carboxylic acid, anhydride, chloride, or activated acid is selected so as to provide for an R$_{13}$ group (i.e., as part of the —NHC(O)R$_{13}$ substituent) which is hydrogen or alkyl of from 1 to 4 carbon atoms optionally substituted with one or more substituents (preferably 1 to 2 substituents) selected from the group consisting of hydroxy, chloro, bromo, and alkoxy of from 1 to 4 carbon atoms, with an appropriate form of an amino acid or polypeptide moiety activated at the acid group as reported by Bodanszky et al[71];

with an aldehyde or ketone (of from 1 to 4 carbon atoms) at controlled pH to form an imine [—N=C(R$_{14}$)$_2$] which upon reduction (e.g., with sodium cyanoborohydride) provides for an alkylamine substituent [i.e., —NHCH(R$_{14}$)$_2$] as reported by Bernotas et al.[73], with a cyclic carbonate such as ethylene carbonate or propylene carbonate which ring opens upon reaction with the amine to form a carbamate group having an HO—alkylene—OC(O)NH— substituent where alkylene is from 2 to 4 carbon atoms as reported by Wollenberg et al.[78], U.S. Pat. No. 4,612,132, with a chloroformate [i.e., ClC(O)OR$_{17}$] in the manner disclosed by Greig et al.[69]. In this case, the chloroformate has an R$_{17}$ group which is alkyl of from 1 to 4 carbon atoms, with O=C(O—C$_6$H$_4$—pNO$_2$)$_2$ which leads to an activated intermediate which is then reacted with an amine (HNR$_{18}$R$_{19}$) to provide for ureas [—NHC(O)NR$_{18}$R$_{19}$] as described by Piekarska-Bartoszewicz et al.[70], with trimethylamine, sulfur trioxide (SO$_3$) so as to form the —NHSO$_3$H group as described by Petitou[76], and with derivatized formic acid or other materials to form a formamide (—NH—CHO)[74] which can be further functionalized to the isocyano (—N=C=O) and reduced to the deoxy derivative by tributyltin hydride (Bu$_3$SnH)[74].

Trisaccharides 7b, 7c, and 7d and derivatives derived therefrom are then fucosylated by contacting the appropriate trisaccharide with βGal(1→3/4)βGlcNAc α(1→3/4) fucosyltransferase in the presence of GDP-fucose so as to provide tetrasaccharides 8b, 8c, and 8d which are analogues of sialyl Lewis$^a$.

Figure 3:
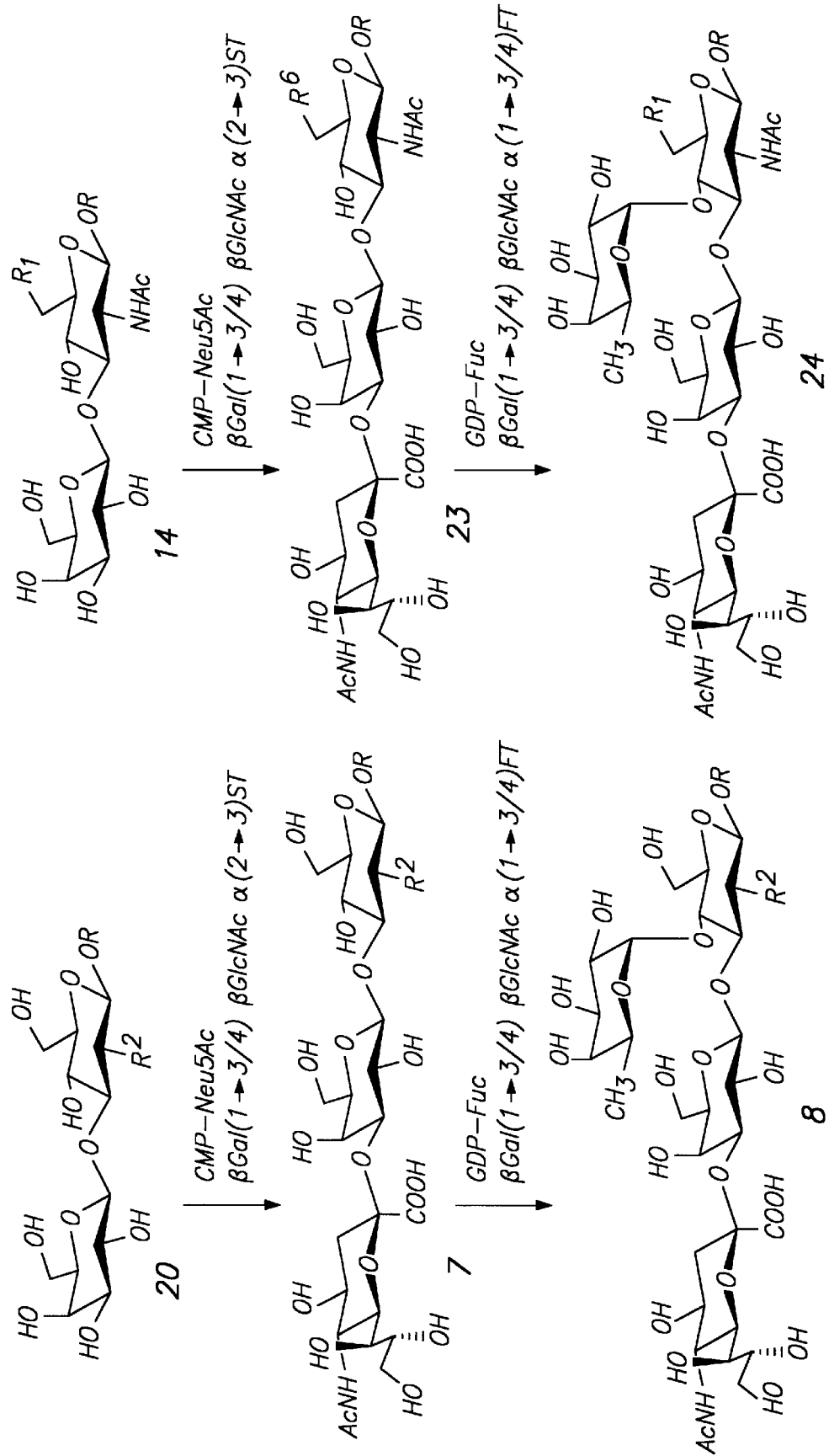
FIG. 3 illustrates an alternative chemo-enzymatic synthesis of analogues of sialyl Lewis$^a$ modified at the C-2 and/or C-6 positions of the N-acetylglucosamine unit.

FIG. 3 illustrates a general scheme for preparing the sialyl Lewis$^a$ analogues of this invention from an appropriately derivatized βGal(1→3)βGlcNAc structure by the sequential enzymatic sialylation and fucosylation of this structure. FIG. 3 only illustrates modification at the 2 or 6 position of the N-acetylglucosamine (GlcNAc) structure. However, it is understood that the modifications can be combined to provide for modification at both the 2 and 6 position of the N-acetylglucosamine. It is further understood that while FIG. 3 illustrates only a 2-hydroxyl group at the 2 position of the galactose, this position may also be substituted with hydrogen or fluoro. Such substituted galactose compounds are known in the art. Substitution of these galactose compounds in the reactions depicted in the figures lead to these modified galactose units in the sialyl Lewis$^a$ analogues.

Enzymatic Sialylation

In FIG. 3, sialylation is accomplished by use of the βGal(1→3/4)βGlcNAc α(2→3)sialyltransferase [i.e., βGal (1→3/4)βGlcNAc α(2→3)ST] but the βGal(1→3)GalNAc α(2→3)sialyltransferase can also be used. The enzymatic transfer of sialic acid onto the 3-position of galactose to form α-sialyl(2→3)βGal requires the prior synthesis (i.e., activation) of its nucleotide (CMP) derivatives. Activation of sialic acid is usually done by using the enzyme CMP-sialic acid synthase which is readily available and the literature provides examples of the activation of various analogues of sialic acid such as 9-substituted Neu5Ac[36,37,38,39–41], 7-epi-Neu5Ac[42], 7,8-bis-epi-Neu5Ac[42], 4-O-methyl-Neu5Ac[43], 4-deoxy-Neu5Ac[44], 4-acetamido-Neu5Ac[46], 7-deoxy-Neu5Ac[40], 4,7-dideoxy-Neu5Ac[40], the 6-thio derivatives of Neu5Ac[45] and Neu5OH (KDN).

The resulting CMP-sialic acid analogue (which in FIG. 3 is illustrated as the CMP derivative of Neu5Ac, i.e., CMP- Neu5Ac) is then combined with the derivatized βGal(1→3)βGlcNAc-OR compound in the presence of the βGal(1→3/4)βGlcNAc α(2→3)sialyltransferase or the βGal(1→3)GalNAc α(2→3)sialyltransferase under conditions wherein sialic acid is transferred to the 3 position of the galactose to form a αNeu5Ac(2→3)βGal linkage. Suitable conditions, known in the art, include the addition of the sialyltransferase to a mixture of the derivatized βGal(1→3)βGlcNAc-OR compound and of the CMP-sialic acid in a appropriate buffer such as 0.1M sodium cacodylate in appropriate conditions of pH and temperature such as at a pH of 6.5 to 7.5 and a temperature between 25° and 45° C., preferably 35°–40° C., while incubating for 12 hours to 4 days. The resulting sialylated product can be isolated and purified using conventional methodology comprising HPLC, ion exchange-, gel-, reverse-phase- or adsorption chromatography.

In regard to the above, it has been shown that with the βGal(1→3/4)βGlcNAc α(2→3) sialyltransferase, substitution of an α-fucose group at the 4 position of the GlcNAc group of the βGal(1→3)βGlcNAc structure prevents the transfer of Neu5Ac to the terminal galactose. On the other hand, substitution of a Neu5Ac at the 6 position of the GlcNAc group of the βGal(1→3)βGlcNAc structure has been reported to permit the transfer of Neu5Ac to the terminal galactose with this sialyltransferase. It has now been found that in assay reactions, affinity purified βGal(1→3/4)βGlcNAc α(2→3)sialyltransferase from rat liver efficiently transfers sialic acid to the 3-position of galactose (compounds 20b,c; 14a,b) modified at the 2 position ($R_2$) or the 6 position ($R_1$) of the GlcNAc unit of βGal(1→3)βGlcNAc-OR. These assays are described in the examples and the results of these assay reactions are set forth in Table I below:

TABLE I

Acceptor specificity of the βGal (1→¾) βG1CNAc α (2→3)-sialyltransferase

| Compound | | | % Rate of Incorp- |
|---|---|---|---|
| No. | $R_2$ | $R_1$ | oration[a] |
| Type I | | | |
| 20a | NHAc | OH | 100 |
| 20b | $N_3$ | OH | 380[b] |
| 20c | $NH_2$ | OH | 260[b] |
| 14a | NHAc | Br | 85[b] |
| 14b | NHAc | H | 43[b] |

[a]measured at 2 mM acceptor concentration
[b]relative to the parent type I (compound 20a-where R = $(CH_2)_8CO_2CH_3$ and $R_2$ = –NHAc, FIG. 3)

The data reported in Table I indicate that derivatives of the βGal(1→3)βGlcNAc-OR structure modified at the 2 or 6 positions of the GlcNAc are active with this sialyltransferase so as to accept sialic acid at the 3 position of the galactose unit and to place a sialic acid group at an α(2→3) position of the galactose. This data further shows that in some cases, the relative rate of transfer of sialic acid onto the modified βGal(1→3)βGlcNAc structure is surprisingly higher than for the unmodified structure.

Enzymatic fucosylation

In FIG. 3, fucosylation is accomplished by use of the βGal(1→3/4)βGlcNAc α(1→3/4)fucosyltransferase [i.e., βGal(1→3/4)βGlcNAc α(1→3/4)FT]. The enzymatic transfer of fucose onto the 4-position of GlcNAc to form αFuc(1→4)βGlcNAc requires the prior synthesis of its nucleotide (GDP) derivatives. Synthesis of GDP-fucose is preferably accomplished in the manner recited by Jiang et al.[34] and which is exemplified in the examples hereunder.

GDP-fucose (GDP-Fuc) is then combined with the sialylated βGal(1→3)βGlcNAc-OR compound in the presence of the βGal(1→3/4)βGlcNAc α(1→3/4)fucosyltransferase under conditions wherein fucose is transferred to the 4 position of GlcNAc of the sialylated βGal(1→3)βGlcNAc compound so as to form a αNeu5Ac(2→3)βGal(1→3)[αFuc(1→4)]βGlcNAc-OR compound (when the sialic acid is αNeu5Ac) derivatized in the βGal(1→3)βGlcNAc backbone. Suitable conditions, known in the art, include the addition of the fucosyltransferase to a mixture of the derivatized αNeu5Ac(2→3)βGal(1→3)βGlcNAc-OR compound (when the sialic acid is αNeu5Ac) and of the GDP-fucose in a appropriate buffer such as 50 mM sodium cacodylate in appropriate conditions of pH and temperature such as at a pH of 6.5 and a temperature between 30° and 45° C., preferably 35°–40° C. while incubating for about 12 hours to 4 days. The resulting sialylated and fucosylated product can be isolated and purified using conventional methodology comprising HPLC, ion exchange-, gel-, reverse-phase- or adsorption chromatography.

In the case of trisaccharides 7b–d, preparative fucosylation of these trisaccharides was performed according to Palcic et al.[22] The products were purified as indicated therein. The structures of trisaccharides 7b–d was confirmed by $^1$H-n.m.r. at 300 MHz (Table II), and those of the resulting sialyl Lewis[a] compounds, 8b–d, by $^1$H-n.m.r. at 500 MHz (Table II) below.

TABLE II

Selected $^1$H-n.m.r. data for compounds: 7b, 7c, 7d, 8b, 8c, 8d[a,b].

| Sugar Unit | Hydrogen | 7b $R^1 = N_3$ | 7c $R^2 = NH_3$ | 7d $R^1 = NHPr$ | 8b $R_2 = N_3$ | 8c $R^1 = NH_3$ | 8d $R^2 = NHPr$ |
|---|---|---|---|---|---|---|---|
| Chemical Shifts (J in Hz) | | | | | | | |
| β-GlcR$^2$ | 1 | 4.550(8.2) | 4.707(8.3) | 4.567$^c$(7.2) | 4.553(8.2) | 4.746 | 4.563(8.5) |
| | 2 | — | 3.176(9.0; 9.5) | — | 3.47 (9.0) | 3.303(9.0; 10.0) | 3.83 |
| | COCH$_2$ | — | — | 2.285(7.5) | — | — | 2.295(7.5) |
| | COCH$_2$CH$_3$ | — | — | 1.131 | — | — | 1.158 |
| α-Fuc | 1 | — | — | — | 4.987(3.5) | 5.077(3.7) | 5.005(3.5) |
| | 2 | — | — | — | 3.76 | 3.78 | 3.78 |

TABLE II-continued

Selected $^1$H-n.m.r. data for compounds: 7b, 7c, 7d, 8b, 8c, 8d[a,b].

| | | Chemical Shifts (J in Hz) | | | | | |
|---|---|---|---|---|---|---|---|
| Sugar Unit | Hydrogen | 7b $R^1 = N_3$ | 7c $R^2 = NH_3$ | 7d $R^1 = NHPr$ | 8b $R_2 = N_3$ | 8c $R^1 = NH_3$ | 8d $R^2 = NHPr$ |
| | 5 | — | — | — | 4.885(6.7) | 4.80[d] | 4.856(6.5) |
| | 6 | — | — | — | 1.179(6.5) | 1.183(6.5) | 1.173 |
| β-Gal | 1 | 4.717 | 4.658(8.0) | 4.485[c](7.6) | 4.846(7.7) | 4.647 | 4.518(7.7) |
| | 2 | — | — | — | 3.54 | 3.67 | 3.51 |
| | 3 | 4.130(2.7; 10.0) | 4.124(3.0; 10.0) | 4.070(3.0; 10.0) | 4.106(2.5; 9.8) | 4.118(2.7; 9.7) | 4.028(3.0; 1( |
| | 4 | — | 3.948 | 3.955(1.0) | 3.93 | 3.94 | 3.90 |
| α-Neu5Ac | 3eq | 2.765(4.5; 12.5) | 2.771(4.5; 12.6) | 2.753(4.7; 12.5) | 2.773(4.4; 12.5) | 2.774(4.5; 12.5) | 2.762(4.5; 1; |
| | 3ax | 1.814(12.2) | 1.782(12.0) | 1.775(12.2) | 1.814(12.0) | 1.785(12.0) | 1.764(12.0 |
| | 4 | — | — | — | 3.67 | — | 3.68 |
| | NHAc | 2.032 | 2.031 | 2.026 | 2.033 | 2.032 | 2.029 |
| | $CH_3CO_2$ | 2.387(7.5) | 2.388(7.5) | 2.390(7.5) | 2.392(7.5) | 2.314(7.5) | 2.389(7.5) |
| | $CO_2CH_3$ | 3.686 | 3.687 | 3.687 | 3.686 | — | 3.686 |

[a]in $D_2O$, with acetone set at 2.225, [b]7b, 7c, 7d: 300 MHz, 8b, 8c, 8d: 500 MHz, [c]interchangeable, [d]overlapped.

In order to ascertain the effect on enzymatic fucosylation at the 4 position of N-acetylglucosamine arising from modification of the 2 or 6 positions of the N-acetylglucosamine of αNeu5Ac(2→3)βGal(1→3)βGlcNAc-OR or βGal(1→3) βGlcNAc-OR the relative rates of fucosylation of compounds 7a, 7b, 7c, and 7d as well as compound 14a were determined. In this regard, compound 14a is synthesized by opening of the benzylidene ring of the known blocked disaccharide 13 with N-bromosuccinimide (FIG. 4) in the presence of either calcium carbonate ($CaCO_3$) or barium carbonate ($BaCO_3$), followed by conventional deprotection of the product leading to disaccharide 14a having a bromo substituent at the 6 position. The deoxy compound 14b can then be prepared as shown in FIG. 5.

The relative rate of transfer of L-fucose to compounds 7a–d and 14a–b by the βGal(1→3/4)βGlcNAc α(1→3/4) fucosyltransferase from human milk was determined at 2 mM acceptor concentration according to Palcic et al.[22] These assays are described in the examples and the results of these assays are summarized in Table III below:

TABLE III

Acceptor specificity of the fucosyltransferase isolated from human milk

| Compound No. | $R_2$ | $R_6$ | Rate of Incorporation[a] % |
|---|---|---|---|
| Type I | | | |
| 7a | NHAc | OH | 100 |
| 7b | $N_3$ | OH | 97 |
| 7c | $NH_2$ | OH | 32 |
| 7d | NHPr | OH | 104 |
| 14a | NHAc | Br | 113 |
| 14b | NHAc | H | 102 |

[a]measured at 2 mM acceptor concentration

The above data demonstrates that modifications at the 2- and the 6-positions of the GlcNAc of the type I structures [βGal(1→3)βGlcNAc] are accepted by the βGal(1→3/4) βGlcNAc α(1→3/4)fucosyltransferase. In addition, the requirement for a free hydroxyl at the 6- position of the terminal galactose had been reported earlier[47]. However, L-fucose can be transferred to derivatives of type I structures where the OH at the 2, 3 and 4 of the β-galactose have been substituted by, for example, specific sugar units attached at these positions which indicates that substitution is possible at the 2-, 3- and possibly the 4-hydroxyls of the terminal β-galactose when using this fucosyltransferase.

Moreover, sialylated trisaccharides modified at the C-2 position of the GlcNAc are surprisingly better acceptors than the corresponding asialo-disaccharides for this fucosyltransferase.

Thus, the three-dimensional topography required by this fucosyltransferase for transfer of L-fucose to the 4 position of the GlcNAc unit of a derivatized βGal(1→3)βGlcNAc structure comprises (1) the 6-hydroxyl group on the galactose unit and the 4-hydroxyl group on the GlcNAc. This knowledge of the βGal(1→3)βGlcNAc specificity for the βGal(1→3/4)βGlcNAc α(1→3/4)fucosyltransferase, or of similar fucosyltransferases from other origins, dramatically increases the usefulness of the versatile enzymes for synthetic purposes.

Consequently, the combined data from Tables I and III demonstrate that the sequential enzymatic transfer of sialic acid and L-fucose to βGal(1→3)βGlcNAc-OR modified at the 2 and/or 6 positions of the GlcNAc, will proceed as in the case of the unmodified (natural) structure. Accordingly, chemical modifications at 2 and 6 positions of GlcNAc unit of βGal(1→3)GlcNAc should lead to compounds that are substrates for the sialyl- and fucosyl-transferases.

As shown below, the analogues of sialyl Lewis$^a$ modified at the 2 and/or 6 positions of the GlcNAc unit can be made by total or partial chemical synthesis of these compounds.

Figures 1, 4:
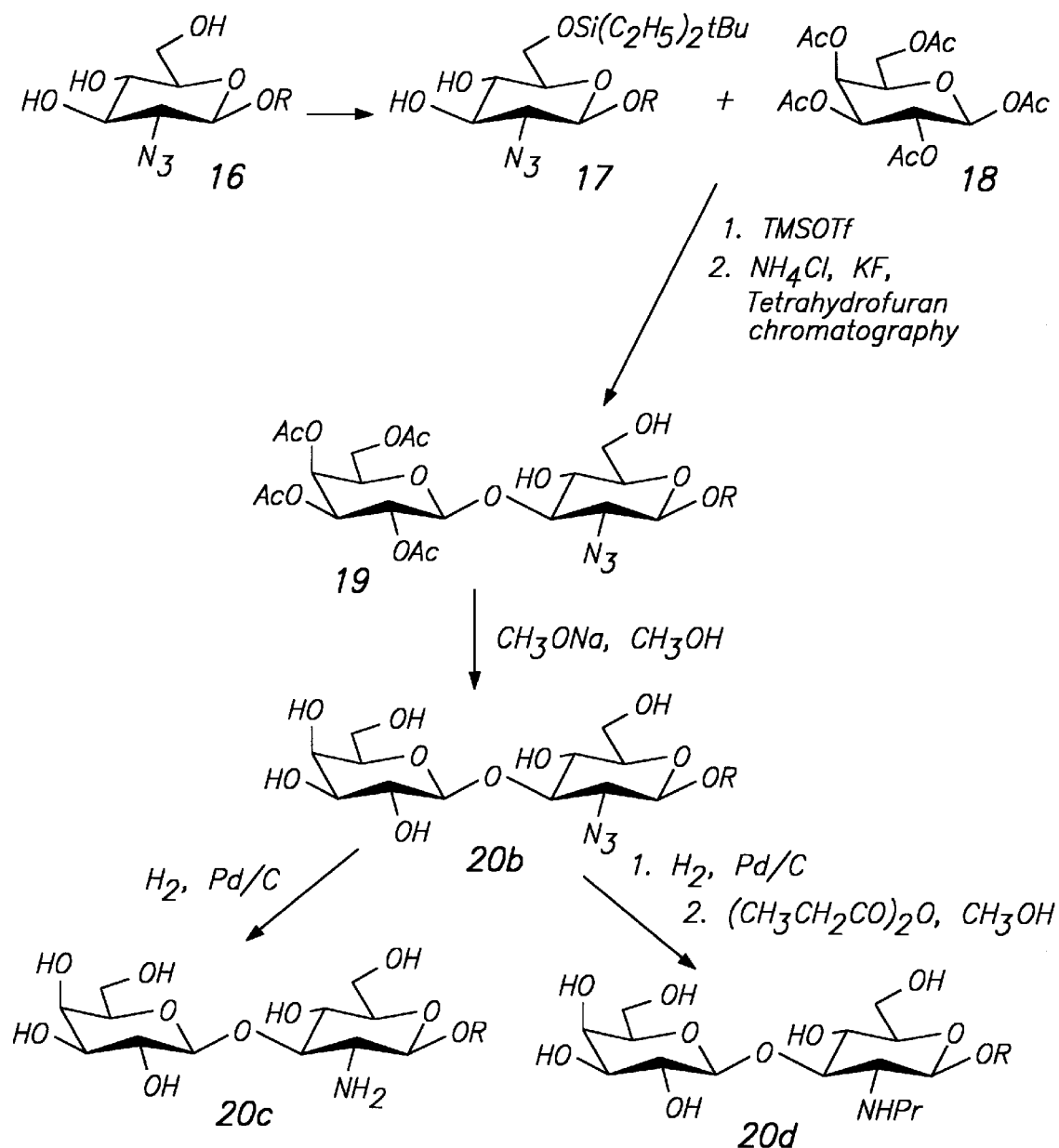
FIGS. 4 and 5 illustrate general schemes for the synthesis of the starting materials used in the preparation of analogues of sialyl Lewis$^a$.
Figures 1, 5:
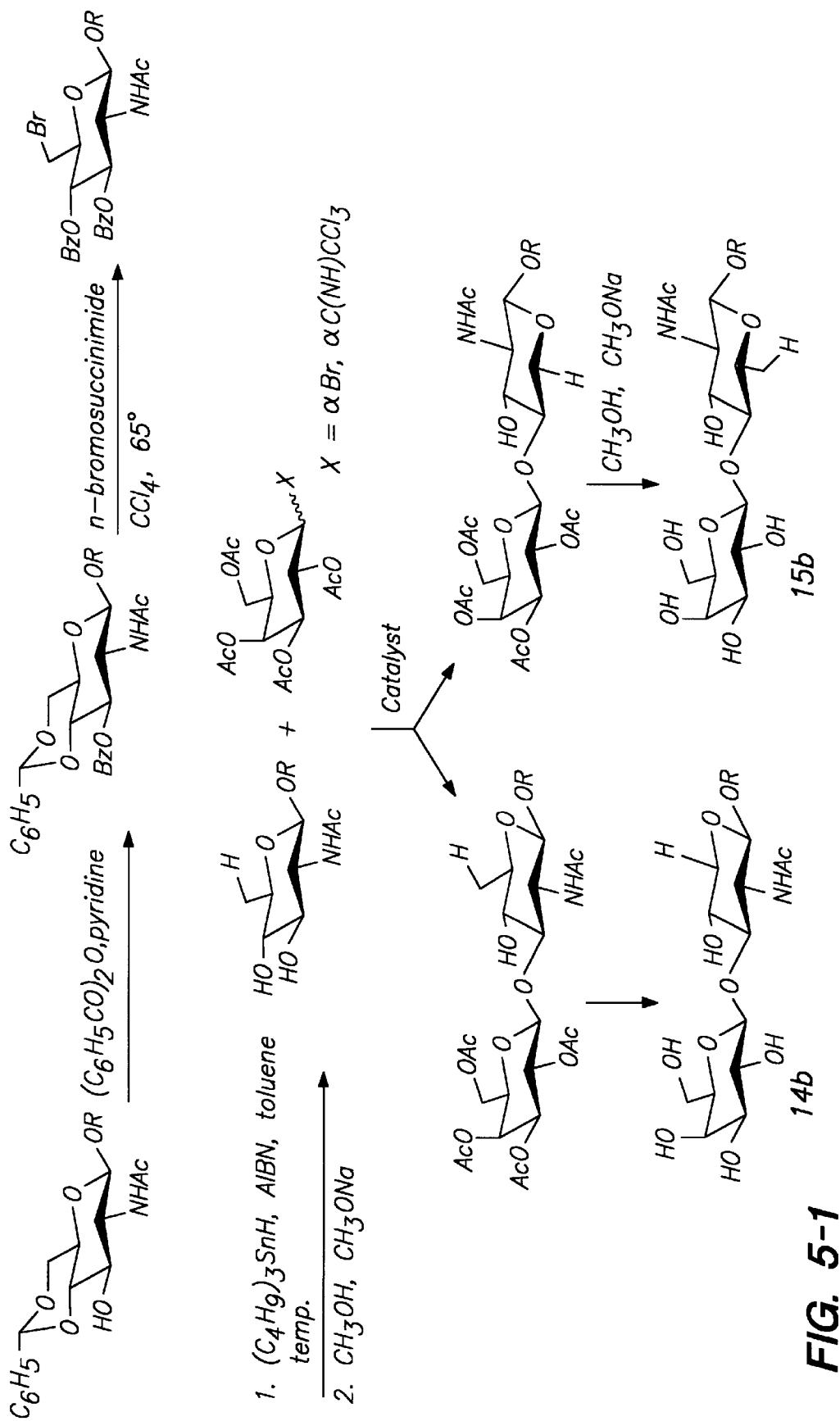
Figures 2, 5:
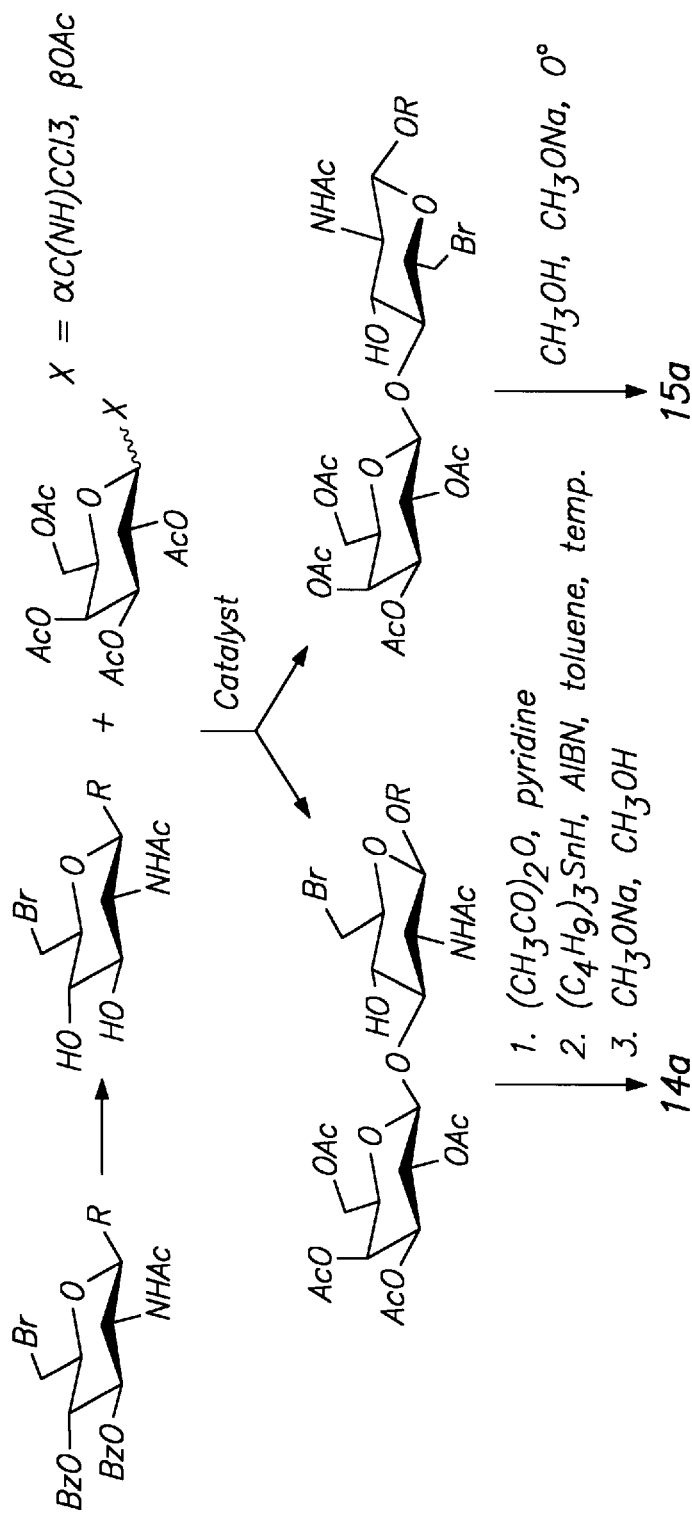

FIG. 4 illustrates the chemical synthesis of specific disaccharide derivatives of βGal(1→3)βGlcNAc starting materials starting with saccharide monomers. In this regard, the chemical coupling of the galactose and GlcNAc units results in the formation of both βGal(1→3)βGlcNAc (type I backbone) and βGal(1→4)βGlcNAc (type II backbone) which can be separated by conventional purification techniques (i.e., chromatography).

Specifically, in FIG. 4, the known[35] 2-azido compound 16 is protected at the 6 position with a removable protecting group (i.e., $Si(C_6H_5)_2tBu$) by conventional techniques[35]. This derivative 17 is then combined with a fully acylated derivative of galactose 18 in the presence trimethylsilyltrifluoromethanesulfonate (TMSOTf) and afterwards ammonium chloride ($NH_4Cl$), potassium fluoride (KF) in tetrahydrofuran are added. The reaction yields a mixture of βGal(1→3)βGlcNAc-OR and βGal(1→4)βGlcNAc-OR derivatives, 19 and 21, which are separated by conventional methods such as chromatography.

Derivative 19 is then deprotected with a mixture of sodium methoxide in methanol ($CH_3ONa/CH_3OH$) to provide for derivative 20b which can be converted to either the amine derivative 20c or the propionate (Pr) derivative 20d following similar procedures set forth above for trisaccharides 7c and 7d.

Alternatively, derivative 19 can be tosylated by conventional techniques to provide for a tosyl group at the 6-position of the GlcNAc derivative. The tosyl derivative can then be used to introduce a 6-halo substituent by a substitution reaction using the appropriate nucleophilic reagent, a 6-alkoxy derivative by alkylation with an alkyl halide in the presence of bis-tributyl tin hydride, and the like.

Additionally, while not shown in FIG. 4, the 2-deoxy ($R_2$=H) and 2-alkoxy glucose derivatives are prepared using a synthetic scheme similar to that recited by Trumtez et al.[74] Specifically, the known 3,4,6-triacylated 1,2-ortho ester of glucose is deacylated under conventional conditions to give the 1,2-ortho ester of glucose. This compound is then converted to the 3,4,6-tribenzyl 1,2-ortho ester of glucose using conventional techniques. The 1,2-ortho ester of the resulting compound is then opened by conventional techniques to provide a protected glycosyl donor such as the 1 α-bromo-2-acetyl-3,4,6-tribenzyl derivative of glucose. This 1 α-bromo derivative is then converted to the glycoside (-OR) by conventional techniques and the 2-acetyl group is then removed. The 2-position is now ready for formation of the 2-deoxy by conventional methods such as first treating with carbon disulfide and methyl iodide in the presence of one equivalent of a base to form the —C(S)$SCH_3$ derivative, followed by reaction with tributyltin hydride) or for the preparation of the 2-alkoxy.

FIG. 5 illustrates the synthesis of the 6-deoxy βGal(1→3) GlcNAc-OR, compound 14b, and the 6-bromo βGal(1→3) GlcNAc-OR, compound 14a. The 6-deoxy compound 14b was synthesized from a known benzylidene ring blocked saccharide (8-methoxycarbonyl-octyl 2-acetamido-4,6-O-benzylidene-2-deoxy-β-D-gluco-pyranoside) which was protected at the 3-hydroxy position with a removable benzoyl blocking group (Bz) by reaction with benzoic anhydride in pyridine. Further conversion of this compound by reaction with N-bromosuccinimide and barium carbonate in carbon tetrachloride ($CCl_4$) at 65° C. leads to the 3,4-dibenzoyl-6-bromo-GlcNAc compound. This compound is, in turn, converted to the 3,4-dibenzyl-6-deoxy-GlcNAc by reaction with $(C_4H_9)_3SnH$ in the presence of AIBN (azo bis-isobutyronitrile) at 110° C. followed by treatment with methanol/sodium methoxide. The resulting 6-deoxy-GlcNAc glycoside is reacted with a known 2,3,4,6-tetraacylated derivative of galactose having an appropriate leaving group at the 1 position to permit formation of a β linkage. Suitable leaving groups include α-bromo and α-trichloroacetamidate [α—C(=NH)$CCl_3$]. The reaction is conducted in the presence of a catalyst which facilitates β linkage formation. Suitable catalysts include silver trifluoromethane sulfonate in the presence of tetra-N-methyl urea when the precursor is a galactosyl bromide; and boron trifluoride ethereate when the donor is galactosyl trichloroacetamidate. The reaction leads to a mixture βGal(1→3) βGlcNAc-OR and βGal(1→4)GlcNAc-OR protected compounds which can be isolated and separated by conventional techniques (e.g., chromatography). Removal of the removal protecting groups then leads to compound 14b.

Alternatively, as also shown in FIG. 5, the 6-bromo-GlcNAc glycoside precursors can be reacted with a known 2,3,4,6-tetraacylated derivative of galactose having an appropriate leaving group at the 1 position to permit formation of a β linkage so as to provide for an alternative route to the 6-bromo compounds (as compared to the route set forth in FIG. 4 for compound 14a). Suitable leaving groups include αC(NH)$CCl_3$ and the reaction is conducted in the same manner as that employed to prepare compound 14b.

Figure 6:
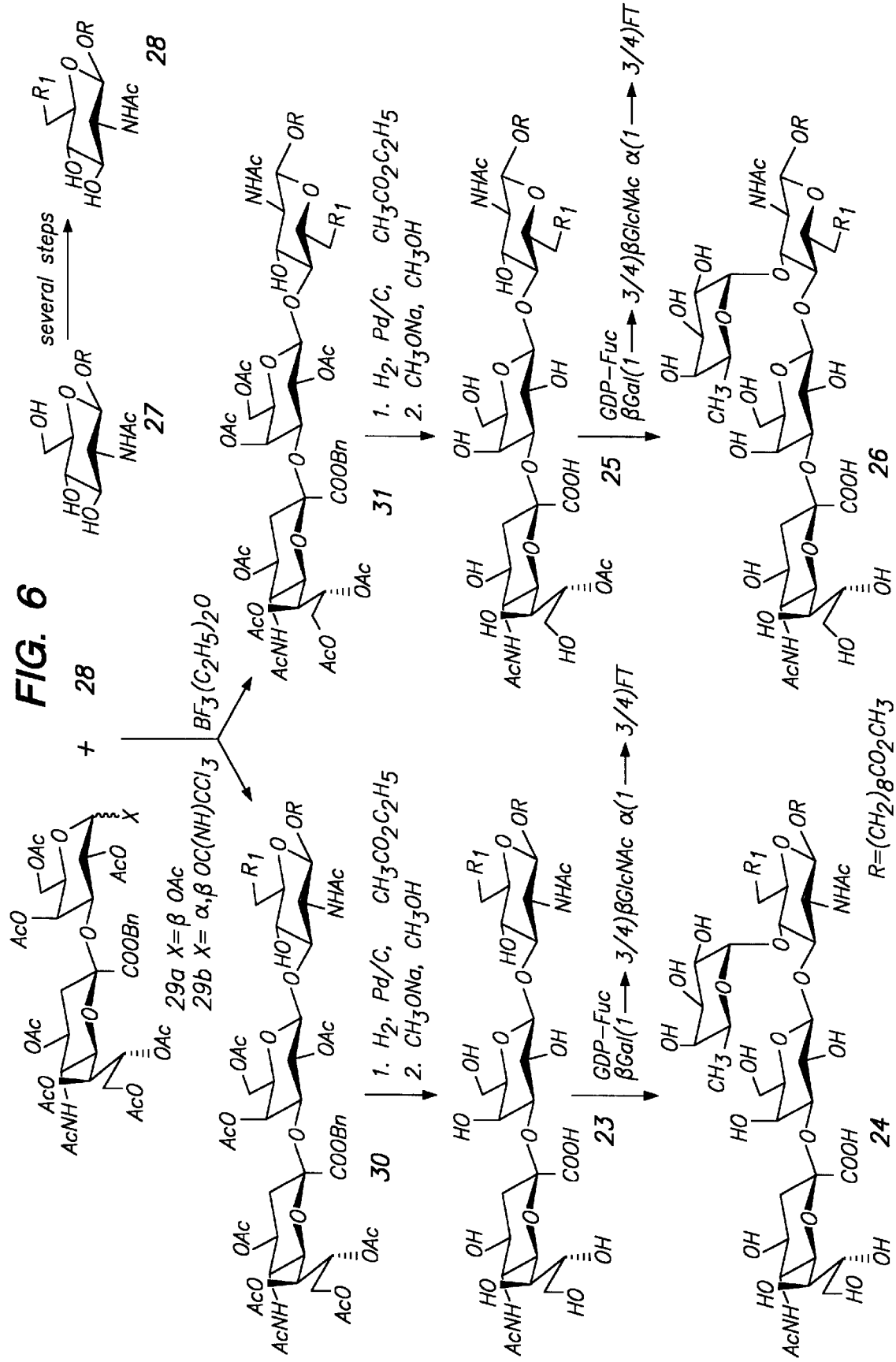
FIG. 6 illustrates a general reaction scheme for the chemo-enzymatic synthesis of analogues of sialyl Lewis$^a$ modified at the C-6 position of the N-acetylglucosamine unit.
Figure 7:
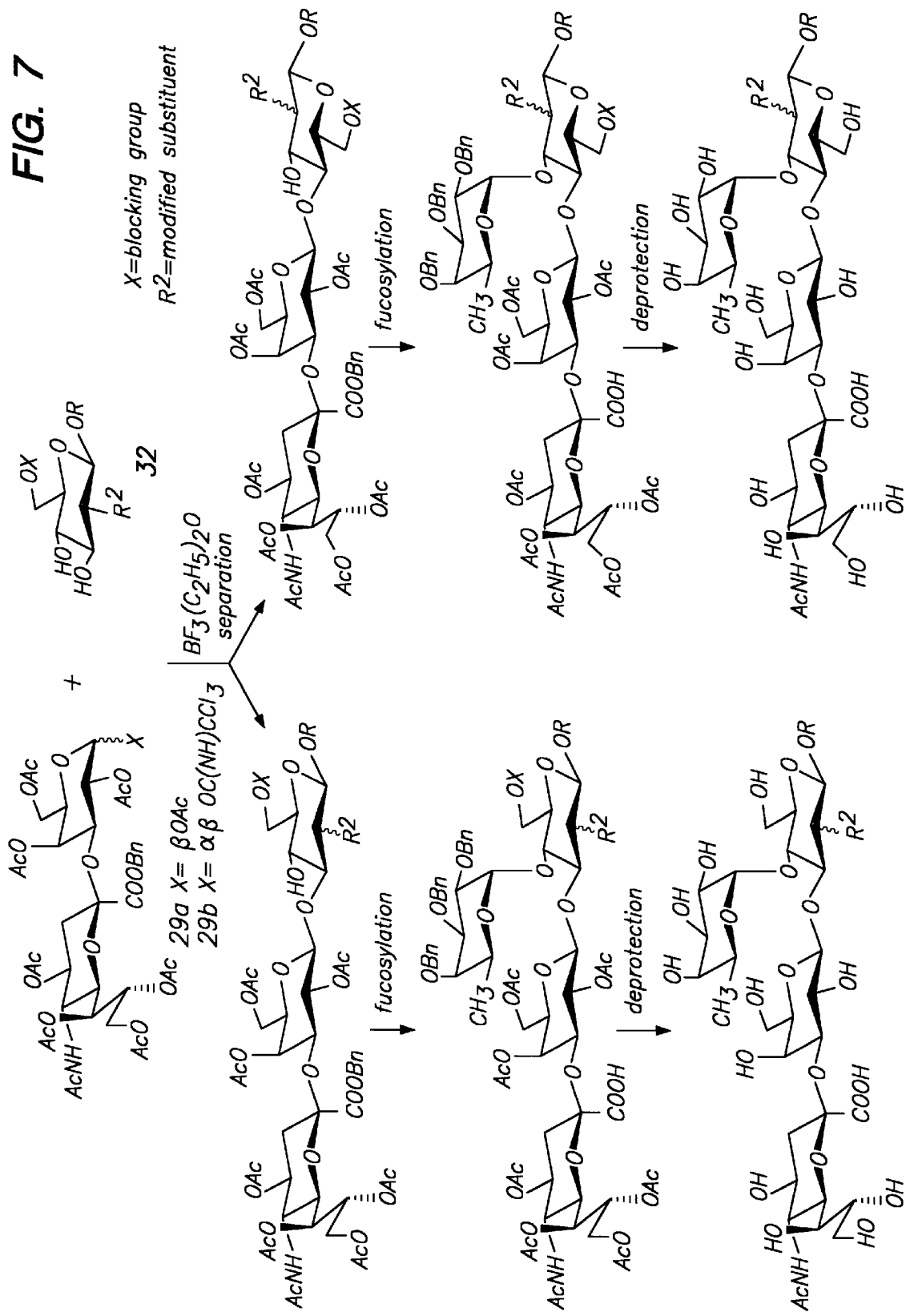
FIG. 7 illustrates a general reaction scheme for the total chemical synthesis of analogues of sialyl Lewis$^a$ modified at the C-2 position of the derivatized N-acetylglucosamine unit.

FIGS. 6 and 7 illustrate the chemical synthesis of α-sialyl (2→3)βGal(1→3)βGlcNAc-OR derivatives modified at the 6-position (FIG. 6) or the 2-position (FIG. 7) of the GlcNAc derivative by using one of the procedures described in Ratcliffe et al.[23,35].

Specifically, as illustrated in FIG. 6, the appropriate 6-substituted derivatives of GlcNAc are prepared as above from either known[51] glycoside 27 or from the known benzylidene ring blocked saccharide protected form depicted in FIG. 5 (which is derived from glycoside 27) as described in detail above. The 6-derivatized blocked material (as depicted in FIG. 5) is then deblocked using conventional methods to provide for modified compound 28 which is a 6-derivative of GlcNAc.

Compound 28 is then combined with disaccharide 29b in the manner known in the art[35] to provide for trisaccharides 30 and 31 having conventional removable blocking groups on the Neu5Ac and the galactose units. Specifically, compound 29b is synthesized from the disaccharide 29a by known methods and is then reacted with compound 28 in the presence of an appropriate catalyst such as [$BF_3$, $(C_2H_5)_2O$ ] to give a mixture of the corresponding β(1→3) or β(1→4) linked trisaccharides 30 and 31, respectively. The ratio of compounds 30:31 will depend upon the nature of the substituent $R_1$ and on the reaction conditions. In any event, trisaccharides 30 and 31 are typically separated and purified by conventional techniques including chromatography. Removal of the blocking groups on trisaccharide 30 is also conventional (i.e., addition of hydrogen in the presence of palladium on carbon followed by treatment with sodium methoxide in the presence of methanol) and leads to the trisaccharide αNeu5Ac(2→3)-βGal(1→3)βGlcNAc-OR 23. Fucosylation of this trisaccharide 23 is preferably conducted with GDP-fucose (GDP-Fuc) in the presence of βGal(1→3/4)βGlcNAc α(1→3/4)-fucosyltransferase [βGal(1→3/4) βGlcNAc α(1→3/4)FT] to lead to sialyl Lewis$^a$ analogues 24 modified at the 6-position of the GlcNAc unit.

When the $R_1$ substituent is azido (—$N_3$—the synthesis of which is described below), this substituent can be further functionalized to other appropriate $R_1$ substituents as described above either at the monosaccharide level (as shown in FIG. 6) or at the trisaccharide 30 level. For example, if the $R_1$ group of trisaccharide 30 is an azido group, then this group can be functionalized in trisaccharide 30 to provide for the amino, amido, imino, etc. substituents described above.

In any event, functionalization is generally at a point in the synthesis where the to-be formed functional group does not interfere with any of the further intended reactions. For example, if an $R_1$ functional group in monosaccharide 28 would interfere with the coupling reaction between disaccharide 29b and monosaccharide 28 then this functional group can be introduced into trisaccharide 30.

In FIG. 7, the appropriate 2-substituted 6-protected derivatives of GlcNAc-OR, compound 32, are prepared, for example, from the known blocked saccharide 17 depicted in FIG. 4.

Compound 32 is then combined with disaccharide 29a or 29b using methods known in the art such as those described by Ratcliffe et al.[35] to provide for trisaccharides having conventional removable blocking groups on the Neu5Ac, on the Gal, and on the 6-position of the GlcNAc units. Specifically, compound 29b is synthesized from the disaccharide 29a and is then reacted with compound 32 in the presence of an appropriate catalyst such as [BF$_3$, (C$_2$H$_5$)$_2$O] to give a mixture of the corresponding β(1→3) or β(1→4) linked trisaccharides, respectively. The ratio of β(1→3) to β(1→4) compounds will depend upon the nature of the substituent R$_2$ and on the reaction conditions. In any event, these trisaccharides are typically separated and purified by conventional techniques including chromatography. Fucosylation of this protected trisaccharide is then accomplished by reaction of the trisaccharide with an appropriate fucosyl donor such as the tetra-O-benzyl fucopyranosyl bromide as recited by Ratcliffe et al.[35] Removal of the blocking groups on the resulting tetrasaccharide is also conventional and leads to sialyl Lewis$^a$ analogues modified at the 2-position of the GlcNAc unit.

Alternatively and in a preferred embodiment, fucosylation is accomplished by contacting the deprotected trisaccharide with GDP-fucose (GDP-Fuc) in the presence of βGal(1→3/4)βGlcNAc α(1→3/4)-fucosyltransferase [βGal(1→3/4) βGlcNAc α(1→3/4)FT] to lead to sialyl Lewis$^a$ analogues modified at the 2-position of the GlcNAc unit.

As noted above, when the R$_2$ substituent is azido (—N$_3$), this substituent can be further functionalized to other appropriate R$_2$ substituents as described above either at the monosaccharide level or at the protected trisaccharide level. For example, if the R$_2$ group of the protected trisaccharide is an azido group, then this group can be functionalized in this trisaccharide to provide for the amino, amido, imino, etc. substituents described above. Functionalization is generally at point in the synthesis where the to-be formed functional group does not interfere with any of the further intended reactions. For example, if an R$_2$ functional group in monosaccharide 32 would interfere with the coupling reaction between disaccharide 29b and monosaccharide 32 then this functional group can be introduced into the protected trisaccharide.

Other derivatives at the 6-position of the GlcNAc can be prepare by art recognized methods and then these compounds can be coupled to the galactose to form βGal(1→3) βGlcNAc-OR derivatives and βGal(1→4)βGlcNAc-OR derivatives which can be separated by conventional techniques (e.g., chromatography). The βGal(1→3)-βGlcNAc-OR derivatives, in turn, can be sialylated and fucosylated as described above, to provide the sialyl Lewis$^a$ derivatives modified at the 6-position.

In regard to the above, compound 28 having a chloro bromo or iodo substituent at the 6 position can be prepared by direct halogenation of the unmodified GlcNAc-OR using the methods reported by Belkhouya et al.[77]

Figure 8:
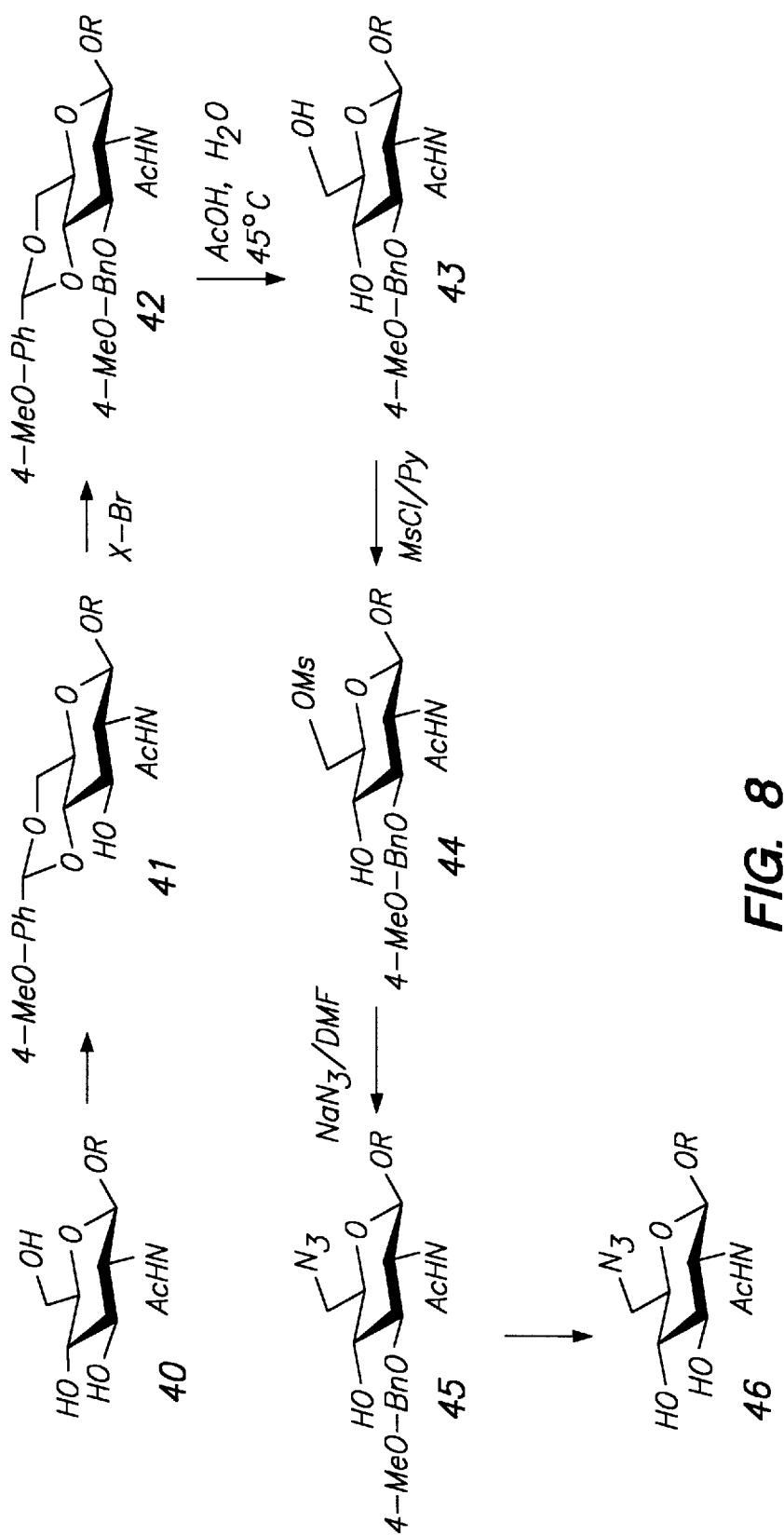
FIG. 8 illustrates a general reaction scheme for preparing the 6-azido derivative of the GlcNAc saccharide unit.

The 6-azido derivatives of GlcNAc-OR can be prepared in the manner described in FIG. 8. Specifically, GlcNAc-OR, compound 40, is converted to the p-methoxybenzylidine blocked compound 41 by reaction with (CH$_3$O)$_2$CH—C$_6$H$_4$—p—OCH$_3$. This compound is then protected at the 3-hydroxyl position by reaction with 4—CH$_3$O—C$_6$H$_4$—CH$_2$Br to provide for compound 42 where X is 4—CH$_3$O—C$_6$H$_4$—CH$_2$—. Compound 42 is partially deprotected at the 4 and 6 positions by reaction with acetic acid (AcOH) in water at about 45° C. to provide for compound 43. The 6-mesylate, compound 44, is prepared by reacting compound 43 with mesyl chloride in pyridine (MsCl/py). The 6-azido derivative, compound 45, is then formed by reaction with sodium azide in dimethylformamide (DMF) and removal of the 3-blocking group with dichloro-dicyanoquinone (DDQ) yields compound 46.

The 6-mesyl compound 44 can be derivatized to any of a number of 6-substituents including halo substituents, alkoxy substituents, ester substituents, etc. by well known chemistry.

The 6-azido compound 45 can be derivatized to the 6-amino at an appropriate point in the synthesis of the sialyl Lewis$^a$ analogue in the manner described above for trisaccharide 3. The 6-amino derivative can then be further functionalized by conventional methods to provide for —H, —NHC(O)R$_6$, —NHSO$_3$H, —N═C(R$_7$)$_2$, —NHCH(R$_7$)$_2$ —N(R$_8$)$_2$, and an amino acid or polypeptidyl residue derivatives by conventional methods. For example, the —NH$_2$ group can be reacted, using conventional techniques, with:

a carboxylic acid, anhydride or chloride to provide for amides (e.g., as per the formation of the propionamide of trisaccharide 7d). Alternatively, the desired acid can be activated, as reported by Inazu et al[72] and then reacted with the amino group. The carboxylic acid, anhydride, chloride, or activated acid is selected so as to provide for an R$_6$ group (i.e., as part of the —NHC(O)R$_6$ substituent) which is hydrogen or alkyl of from 1 to 4 carbon atoms optionally substituted with one or more substituents (preferably 1 to 2 substituents) selected from the group consisting of hydroxy, chloro, bromo, and alkoxy of from 1 to 4 carbon atoms, with an appropriate form of an amino acid or polypeptide moiety activated at the acid group as reported by Bodanszky et al.[71];

with an aldehyde or ketone (of from 1 to 4 carbon atoms) at controlled pH to form an imine [—N═C(R$_7$)$_2$] which upon reduction (e.g., with sodium cyanoborohydride) provides for an alkylamine substituent [i.e., —NHCH(R$_7$)$_2$] as reported by Bernotas et al.[73], with a cyclic carbonate such as ethylene carbonate or propylene carbonate which ring opens upon reaction with the amine to form a carbamate group having an HO—alkylene—OC(O)NH—substituent where alkylene is from 2 to 4 carbon atoms as reported by Wollenberg et al.[78], U.S. Pat. No. 4,612,132, with a chloroformate [i.e., ClC(O)OR$_{10}$] in the manner disclosed by Greig et al.[69]. In this case, the chloroformate has an R$_{10}$ group which is alkyl of from 1 to 4 carbon atoms, with O═C(O—C$_6$H$_4$—pNO$_2$)$_2$ which leads to an activated intermediate which is then reacted with an amine (HNR$_{11}$R$_{12}$) to provide for ureas [—NHC(O)NR$_{11}$R$_{12}$] as described by Piekarska-Bartoszewicz et al.[70], with trimethylamine, sulfur trioxide (SO$_3$) at pH 9.5 so as to form the —NHSO$_3$H group as described by Petitou[76], and with derivatized formic acid or other materials to form a formamide (—NH—CHO)[74] which can be further functionalized to the isocyano (—N═C═O) and reduced to the deoxy derivative by tributyltin hydride (Bu$_3$SnH)[74].

Figure 9:
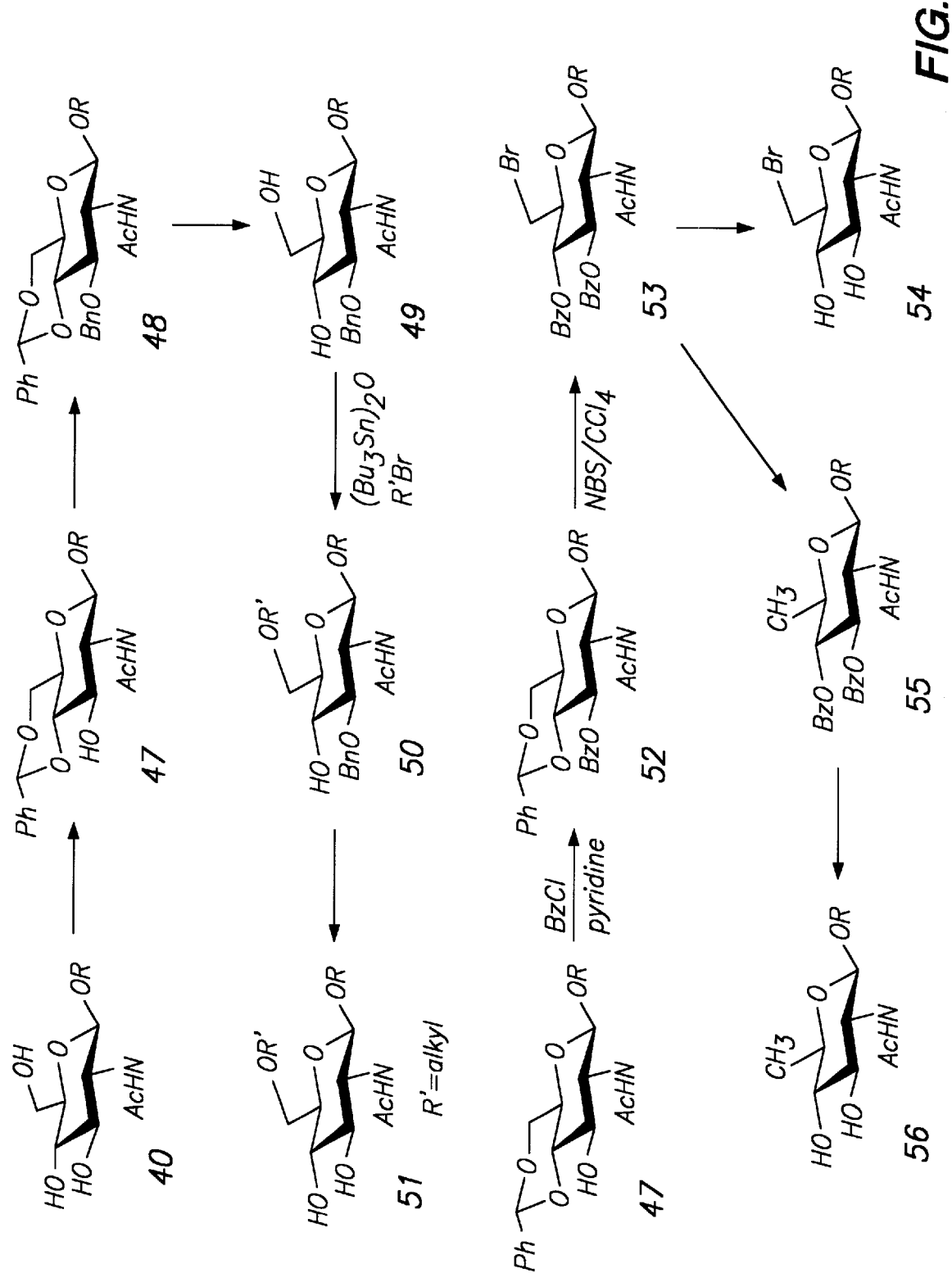
FIG. 9 illustrates a general reaction scheme for introducing the 6-bromo, 6-alkoxy, and 6-deoxy derivatives at the 6-position of GlcNAc saccharide unit.

The 6-alkoxy, 6-bromo, and 6-deoxy derivatives of GlcNAc can be prepared in the manner described in FIG. 9. Specifically, GlcNAc-OR, compound 40, is reacted with C$_6$H$_5$CH(OCH$_3$)$_2$ in an acidic medium in acetonitrile to provide for the 4,6-diprotected benzylidine compound 47. In turn, compound 47 can be reacted with benzyl (Bn) bromide and sodium hydride in the presence of dimethylformamide at around 0° C. to provide for a benzyl protecting group at the 3-position, i.e., compound 48. Deprotection at the 4,6 positions by contacting compound 48 with acetic acid and water at about 80°–90° C. provides for compound 49. Reaction of compound 49 with dibutyltin oxide [(Bu)$_2$SnO] and R$_9$Br provides for the 6-alkoxy compound 50. Conventional deprotection of the benzyl group with hydrogen in palladium/carbon yields compound 51.

In another embodiment, compound 47 can be reacted with [C$_6$H$_5$C(O)]$_2$O in pyridine to provide for a benzoyl protecting group (Bz) at the 3-position, i.e., compound 52. Reaction of compound 52 with N-bromosuccinimide in carbon tetrachloride yields the 6-bromo compound 53 which after conventional deprotection of the benzoyl groups with sodium methoxide in methanol gives the 6-bromo compound 54.

Alternatively, compound 53 can be reacted with tributyltin hydride [(Bu)$_3$SnH] in toluene to provide for the 6-deoxy compound 55 which after conventional deprotection of the benzoyl groups with sodium methoxide in methanol gives the 6-deoxy compound 56.

The 6-SR$_8$ compounds are prepared from the 6-mesyl derivative, compound 44, by reaction with potassium thioacetate, $CH_3C(O)S^-K^+$, to give the thioacetate derivative at the 6-position. This derivative is then treated with mild base to produce the 6-SH derivative. The 6-SH can be reacted with an alkyl halide (e.g., $CH_3Br$) to provide the 6-SR$_8$ derivatives which, in turn, can be partially or fully oxidized to the 6-sulfone or the 6-sulfoxide derivaties, —S(O)R$_8$ and —S(O)$_2$R$_8$ where R$_8$ is alkyl of from 1 to 4 carbon atoms.

The 6-fluoro compound is prepared from known chemistry[79] by reacting compound 49 with mesyl chloride in pyridine to form the 6-mesylate which upon reaction with tetraethylammonium fluoride provides for the 6-fluoro derivative. Deprotection of the 3 benzyl group by hydrogen and palladium on carbon gave the 6-deoxy 6-fluoro derivative of compound 40.

The above reaction schemes depict a number of 2- or 6-substituted derivatives of GlcNAc. However, it is apparent that these modifications can be combined to provide for substituents at both the 2- and 6-positions. When disubstitution is desired, the modifications are conducted at an appropriate point in the synthesis so as to be compatible with each other. That is to say that modification at the 2-position must be made with respect to the modification at the 6-position. This is within the ordinary skill of the art.

B2. Coupling of Sialyl Lewis$^a$ Analogues to Antigenic Carriers i. Coupling of a Sialyl Lewis$^a$ Derivative to an Artificial Carrier Procedures for coupling (linking) oligosaccharide glycosides containing an aglycon having a functional group capable of linking to antigenic carrier so as to form an artificial antigen are documented in the literature[49,50]. In general, such antigenic carriers contain at least one complementary reactive functional group which will react with the functional group on the aglycon (or a derivative thereof). Care should be taken to ensure that the functional groups and the coupling procedure employed are compatible with the nature of the sialyl Lewis$^a$ analogue used and, in particular, with the functional groups present on this analogue (e.g., at the 2 and/or 6 position of the N-acetylglucosamine unit as well as the carboxylic group on the sialic acid unit). One suitable coupling procedure documented in the art employs a ester functionality (COOR' where R' is a leaving group or is transformable into a leaving group such as an alkyl of from 1 to 6 carbon atoms) on the aglycon which is transformed into an acyl azide (—CON$_3$) following known procedures. The azide can then be coupled to an antigenic carrier following known procedures[51,52].

Another suitable procedure employs an aglycon moiety having a terminal ethylenic group, preferably an activated terminal ethylenic group, such as an allyloxy group —O—$CH_2CH$=$CH_2$, which can then be activated by known methods in order to effect coupling to the carrier[53,54].

Once the aglycon functional group of the sialyl Lewis$^a$ analogue has been activated, the coupling reaction is generally conducted by adding a molar amount or a substantial molar excess of this oligosaccharide glycoside to a composition containing the carrier under conditions whereby the functional group(s) or activated functional groups (if activation is necessary) on the aglycon react with a complementary reactive functional groups on the carrier. The amount of the sialyl Lewis$^a$ analogue added in conjunction with the number of reactive sites on the carrier dictates the number of such analogues attached to each carrier and this number will vary with the selected carrier. In general, sufficient sialyl Lewis$^a$ analogues are added so as to provide at least 1 such substituent per carrier. Preferably, the number of substituents is from 1 to about 60 per each carrier and more preferably, the number of substituents is from about 1 to about 20 per each carrier.

The examples herein below present procedures for coupling a carrier having a reactive functional group to a sialyl Lewis$^a$ analogue having a complementary reactive functional group on the aglycon moiety or a functional group on the aglycon moiety which is capable of being activated (derivatized) to a complementary reactive functional group. These examples are non-limiting.

ii. Coupling of a βGal(1→3)βGlcNAc-OR Derivative to an Artificial Carrier followed by Sialylation and Fucosylation As noted above, the coupling reactions useful in linking the sialyl Lewis$^a$ analogues to the artificial antigen is limited by the fact that the coupling reaction employed must not affect the functional groups on the sialyl Lewis$^a$ analogue in an unintended manner (e.g., at its —COOH group on the sialic acid). To circumvent this restriction, it may be advantageous to first couple the βGal(1→3)βGlcNAc derivative to the antigenic carrier via its aglycon functionality and then, in a sequential manner, enzymatically transfer sialic acid and fucose to the βGal(1→3)βGlcNAc derivatives attached to the artificial antigen so as to provide for artificial antigens having pendent thereto one or more sialyl Lewis$^a$ analogues.

In this embodiment, the coupling of the asialo oligosaccharide glycoside to the antigenic carrier is achieved in the same manner as described above. Likewise, the enzymatic transfer of sialic acid and fucose to the βGal(1→3)βGlcNAc derivatives attached to the artificial antigen is also achieved in the same manner as described above.

iii. Coupling of Sialyl Lewis$^a$ Analogues to Carriers other than Antigenic Carriers Small molecular weight carriers could provide di-, tri- or multivalent haptens with increased inhibitory potency. Appropriate sialylated Lewis$^a$ polymeric carriers or co-polymerization of a sialyl Lewis$^a$ monomer with an appropriate monomer could lead to non-immunogenic or biocompatible products. Artificial liposomes or micelles could be used as antigens, drug carriers or multivalent inhibitors. Accordingly, in addition to coupling to antigenic carriers, the sialyl Lewis$^a$ analogues described herein can be coupled to or incorporated with other carriers. For example, if the aglycon moiety of such oligosaccharide glycosides contains a hydrophobic group, then the oligosaccharide glycosides can be incorporated into micelles and liposomes.

Liposomes and micelles containing sialyl Lewis$^a$ analogues are useful for antigens or inhibitors of cellular adhesion phenomena/targeting.

Similarly, the carrier employed can be a solid phase particle containing one or more reactive functionalities and this can be reacted with one or more sialyl Lewis$^a$ analogues containing a complementary reactive functional group on the aglycon which results in coupling to the solid phase particle so that the solid phase particle contains at least one conjugated sialyl Lewis$^a$ analogue. Such coupling would proceed in a manner similar to that described above. In this embodiment, the resulting solid phase particles would be useful in isolating enzymes (not sialyltransferases) lectins or other biological receptors from an aqueous solution containing such materials. Solid phase particles containing reactive functional groups are well known in the art and include Sepharose, aminopropyl-silica, aminopropyl-CPG (controlled pore glass), amino-ethyl cellulose, Trisacryl$^R$-NH, glass beads, polyacryl-amide particles, and the like.

The sialyl Lewis$^a$ analogues can also be coupled to larger molecular weight carriers of a polymeric nature which are chosen for their properties such as non-immunogenicity, bio-compatibility and the ability to incorporate numerous sialyl Lewis$^a$ analogues per molecule of carrier.

Solid phase and polymeric carriers containing one or more sialyl Lewis$^a$ analogues are also useful, for example, in competitive immunoassays wherein the solid phase or polymeric carriers are added to a sample suspected of containing the natural substance. Antibodies raised against the sialyl Lewis$^a$ analogues and which cross-react with the natural substance are then added to the sample. Such antibodies are appropriately labeled so as to provide a detectable signal. The degree of binding of the labeled antibody to the solid phase or polymeric carrier depends on the amount of natural substance found in the sample. After incubation, the solid phase or polymeric carrier is then isolated from the sample and the amount of antibody bound to the carrier is ascertained by measuring the signal level. Correlation of the measured signal to standards permits an assessment of the level of natural antigen in the sample.

Additionally, non-immunogenic conjugates would be useful as inhibitors of cellular adhesion phenomena where multivalent conjugates are contemplated to be more effective inhibitors than monovalent haptens.

C. Utility

The sialyl Lewis$^a$ analogues described herein are useful for the treatment of diseases, including treating cell-mediated immune responses to an antigen including, by way of example, modulating cell-mediated inflammatory responses, and the like.

The sialyl Lewis$^a$ analogues described herein are effective in suppressing cell-mediated immune responses to an antigen when administered at a dosage range of from about 0.5 mg to about 50 mg/kg of body weight, and preferably from about 0.5 to about 5 mg/kg of body weight. The specific dose employed is regulated by the particular cell-mediated immune response being treated as well as by the judgement of the attending clinician depending upon factors such as the severity of the adverse immune response, the age and general condition of the patient, and the like. The sialyl Lewis$^a$ analogues can be administered orally, parenterally, rectally, transdermally, etc. Preferably, the sialyl Lewis$^a$ analogues are administered parenterally.

Because suppression of cell-mediated immune responses by the sialyl Lewis$^a$ analogues requires initiation of the immune response, the sialyl Lewis$^a$ analogues are generally administered to the patient at least about 0.5 hours after onset of the immune response and, preferably, at least about 1 hour after, and most preferably, at least about 5 hours after onset of the immune response.

In addition to modulating a cell-mediated immune response to an antigen, administration of the sialyl Lewis$^a$ analogues also impart a degree of tolerance to additional challenges from the same antigen. In this regard, re-challenge by the same antigen weeks after administration of the sialyl Lewis$^a$ analogue results in a significantly reduced immune response (i.e., suppression of a cell-mediated immune response). Thus, administration of the sialyl Lewis$^a$ analogue simultaneously imparts modulation (e.g., suppression) of a cell-mediated immune response to an antigen and tolerance to future challenges with that antigen.

The methods of this invention are generally achieved by use of a pharmaceutical composition comprising a pharmaceutically acceptable carrier and an effective amount of a sialyl Lewis$^a$ analogue. The pharmaceutically acceptable carrier includes, by way of example, water, buffered saline, etc. The effective amount of a sialyl Lewis$^a$ analogue are those amounts which provide the above-noted dosage of the oligosaccharide glycoside when administered to a patient. It is contemplated that suitable pharmaceutical compositions can additionally contain optional components such as an adjuvant, a preservative, etc.

It is also contemplated that suitable pharmaceutical compositions can include transdermal compositions or bandages which are well known in the art.

Additionally, when attached to antigenic carriers, the sialyl Lewis$^a$ analogues described herein are useful as artificial antigens. Accordingly, such analogues act as intermediates in the preparation of artificial antigens.

The artificial antigens containing the sialyl Lewis$^a$ analogues described herein can be injected into mice, for example, so as to produce antibodies which cross-react with the natural substance. Such antibodies can be used in immunoassay techniques for the purpose of determining the presence and/or level of the natural substance in a sample suspected of containing the natural substance.

In addition to the above, such antibodies (particularly monoclonal antibodies) can be used in antibody therapy for a particular natural antigen (i.e., a natural substance). Specifically, artificial antigens containing one or more of the sialyl Lewis$^a$ analogues described herein, may have one or more antigenic determinants located on the sialyl Lewis$^a$ analogue which may be similar to an antigenic determinant in the natural antigen. When injected into mice, the artificial antigen produces antibodies which cross-react with the natural antigen. Such antibodies can then be collected and employed in antibody treatment for the natural antigen. Preferably, the antibodies are monoclonal antibodies. Methods of isolating a hybridoma line which generates monoclonal antibodies which recognize the antigenic determinant of the artificial antigen containing sialyl Lewis$^a$ analogues and which cross-react with a similar antigenic determinant on the natural antigen are well known in the art. Optionally, such antibodies can be coupled to therapeutic agents to enhance their therapeutic effectiveness.

Likewise, utility for artificial conjugates other than artificial antigens has been set forth above.

The following examples are offered to illustrate this invention and are not to be construed in any way as limiting the scope of this invention.

In these examples, unless otherwise defined below, the abbreviations employed have their generally accepted meaning:

| | | |
|---|---|---|
| AB | = | AB pattern |
| ATP | = | Adenosine tri-phosphate |
| ax | = | axial |
| BSA | = | bovine serum albumin |
| bt | = | broad triplet |
| CDP | = | Cytidine di-Phosphate |
| d | = | doublet |
| dd | = | doublet of doublets |
| ddd | = | doublet of doublets of doublets |
| DTH | = | delayed-type hypersensitivity |

| | | |
|---|---|---|
| eq | = | equatorial |
| i.r. | = | infra red |
| KLH | = | Keyhole Limpet Hemocyanin |
| m | = | multiplet |
| q | = | quartet |
| s | = | singlet |
| t | = | triplet |
| t.l.c. | = | thin layer chromatography |
| U | = | Units |
| μm | = | microns |
| AG 1 × 8 (formate form) | = | ion exchange resin AG 1 × 8 (formate form) available from Bio-Rad Laboratories, Richmond, CA |
| Dowex 50 × 8 ($H^+$ form) | = | ion exchange resin Dowex 50 × 8 ($H^+$ form) available from Dow Chemical, Midland, MI |
| IR-C50 resin ($H^+$ form) | = | ion exchange resin IR-C50 ($H^+$ form) available from Rohm & Haas, Philadelphia, PA |

Commercially available components are listed by manufacturer and where appropriate, the order number. Some of the recited manufacturers are as follows:

Amersham=Amersham Canada Limited, Ontario, Canada
BioRad=Bio-Rad Laboratories, Richmond, Calif.
Iatron=Iatron Laboratories, Tokyo, Japan
Merck=E. Merck AG, Darmstadt, Germany
Millipore=Millipore Corp., Bedford, Mass.
Pel-Freeze Biologicals=Pel-Freez, Rogers, Ark.
Pharmacia=Pharmacia Biosystems Inc., Piscataway, N.J.
Serva=Serva Feinbiochemica, Heidelberg, Germany
Sigma=Sigma Chemical Company, St. Louis, Miss.
Waters=Waters Associates, Inc., Milford, Mass.

EXPERIMENTAL
General Methods

Pre-coated plates of silica gel (Merck, 60-$F_{254}$) were used for analytical t.l.c. and spots were detected by charring after spraying with a 5% solution of sulfuric acid in ethanol. Silica gel 60 (Merck, 230–400 mesh) was used for column chromatography. Iatrobeads were from Iatron (Order No. 6RS-8060). Millex-GV filters (0.22 μm) were from Millipore. $C_{18}$ Sep-Pak cartridges and bulk $C_{18}$ silica gel were from Waters Associates.

Commercial reagents were used in chemical reactions and solvents were purified and dried according to usual procedures. Unless otherwise noted, the reaction mixtures were processed by dilution with dichloromethane and washing with a dilute solution of sodium bicarbonate followed by water. After drying over magnesium sulfate, the solvents were removed by evaporation under vacuum with a bath temperature of 35° C. or lower when necessary.

$^1$H-n.m.r. were recorded at 300 MHz or 500 MHz with either tetramethylsilane in $CDCl_3$ or acetone set at 2.225 in $D_2O$ as internal standards, at ambient temperature, unless otherwise noted. The chemical shifts and coupling constants (observed splitting) were reported as if they were first order, and only partial n.m.r. data are reported. $^{13}$C-n.m.r. spectra were recorded at 75.5 MHz with tetramethylsilane in $CDCl_3$ or dioxane set at 67.4 in $D_2O$ as reference.

Frozen rat livers were from Pel-Freeze Biologicals. CMP-[$^{14}$C]Neu5Ac was obtained from Amersham. Sepharose 6B, Dowex 1-X8 were from Pharmacia, CDP and CMP-Neu5Ac were from Sigma, and ACS liquid scintillation cocktail from Amersham. GDP-fucose was obtained by chemical synthesis as described below. All other chemicals were of analytical grade and of commercial origin.

PREPARATIVE EXAMPLE A
Preparation of the βGal(1→3/4)-βGlcNAc α(2→3) sialyltransferase The βGal(1→3/4)βGlcNAc α(2→3)sialyltransferase [(EC 2.4.99.5)—sometimes referred to as "α(2→3)ST"] and the βGal(1→4)βGlcNAc α(2→6)sialyltransferase [(EC 2.4.99.1)—sometimes referred to as "α(2→6)ST"] were extracted from rat liver (600 g) using Triton CF-54 (Sigma) according to Weinstein et al.[56] The enzymes from the Triton extract were partially purified and concentrated on Cibacron Blue F3GA-Sepharose by a reported modification[59] of Sticher et al.'s process.[57] The detergent extract (3L, 3.5 mg protein/ML) was loaded onto a column (8×20 cm) of Cibacron Blue F3GA (Serva) linked to Sepharose 6B (prepared according to Dean and Watson[58]) equilibrated in 10 mM sodium cacodylate (pH 6.5), 0.15M NaCl, 25% glycerol, 0.1% Triton CF-54 (buffer A) in two portions, with a wash step in between with buffer A. The column was washed with the same buffer until no further protein was eluted, and was then eluted with buffer A containing 2.0M NaCl. Active fractions containing sialytransferases were pooled, concentrated by ultrafiltration on an Amicon PM 30 membrane and dialyzed against 200 volumes of buffer A. The α(2→3)ST was separated from the α(2→6)ST and purified by affinity chromatography on a matrix ($Le^c$-Sepharose) obtained by covalently linking the hapten βGal(1→3)βGlcNAcO($CH_2$)$_8$COOH disclosed by Mazid et al.[59] to activated Sepharose described by Matsumoto[80] using art recognized techniques involving the N-succinimidyl ester of the hapten. The sialytransferases, partially purified by the above dye chromatography, containing ~160 mU of α(2→3)-ST and 2.4 U of α(2→6)ST (about 860 mg protein) were diluted with an equal volume of buffer A containing 2.5 mM CDP at a flow rate of 5 mL/h. The column was washed with the equilibrating buffer to remove any loosely bound protein. Enzyme activity determination indicted that the α(2→3)ST adsorbed strongly to the column during application and subsequent wash steps, while the bulk of the inert protein and the α(2→6)ST eluted unretarded. The α(2→3)ST was then eluted from the column with buffer A containing 0.2M lactose. Fractions (2 mL each) containing the α(2→3)ST were pooled and concentrated to a small column (~1 mL) on an Amicon PM 30 membrane. The concentrate was dialyzed against 200 volumes of 50 mM sodium cacodylate (pH 6.5), 0.25M NaCl, 50% glycerol, 0.1% Triton CF-54 and stored at −20° C. This preparation, 82,000-fold purified to a specific activity of 2.7 U/mg protein, was devoid of α(2→6)ST activity when preparative sialylation using βGal(1→4)βGlcNAc-O-($CH_2$)$_8$COOCH$_3$ (compound 22a) as the acceptor[21] was carried out and the product analyzed by $^1$H-n.m.r. spectroscopy and by t.l.c.

Enzyme Assays

Sialyltransferase activities were assayed following standard methodologies[56]. The activities of the α(2→3)ST and the α(2→6)ST were determined in identical reaction mixtures with the exception of their acceptor substrates, which were compounds 20a and 22a (compound 22a corresponds to the βGal(1→4)βGlcNAc of compound 20), respectively. Incubation mixtures contained, in a total volume of 60 μL, 9 nmol CMP-[$^{14}$C]Neu5Ac (Amersham) (3,340 cpm/nmol), 2 mM acceptor substrate, 1 mg/mL BSA, and enzyme (0–0.2 mU) in 25 mM sodium cacodylate (pH 6.5) containing 0.5% Triton CF-54. After incubation at 37° C. (10–30 min.), radioactive product was isolated by the procedure using Sep-Pak $C_{18}$cartridges[60] (Waters). The cartridge was washed with water (30 mL) until background counts were obtained in the washes. Radiolabelled product was then eluted with methanol (2×5 mL) and quantitated in ACS scintillation cocktail (10 mL) with a Beckman LS-3801 scintillation counter. One unit of enzyme activity is defined as 1 μmol of product formed per minute of incubation at saturating substrate concentrations. Protein concentrations were estimated using the method of Bradford[61].

Sialyltransferase Kinetics

Initial transfer rates of the rat liver α(2→3)ST were determined at a fixed concentration of oligo-saccharide acceptor substrate (2 mM) using reported methodologies[56, 22]. The standard incubation mixtures contained, in a total volume of 60 μL, 560 μU CMP-[$^{14}$C]-Neu5Ac (30,000 c.p.m.), 2 mM acceptor substrate, 1 mg/mL BSA and 360 μU of enzyme in 25 mM sodium cacodylate buffer (pH 6.5) containing 0.5% Triton CF-54. After 30 min. of incubation at 37° C., the reaction was terminated by addition of 50 μL of 10 mM CTP. The radiolabelled product was isolated by the Sep-Pak method[60] for acceptors with the hydrophobic 8-methoxycarbonyloctyl aglycone, or by ion-exchange chromatography on Dowex 1×8 ($PO_4^{2-}$, 100–200 mesh) for acceptors with the other aglycone as described by Paulson et al.[62]. Initial rates are expressed as a percentage with respect to the value obtained with βGal(1→3)βGlcNAc-OR for the α(2→3)ST. In all cases, less than 15% of the CMP-[$^{14}$C]-Neu5Ac was transferred to the product and the assays were performed in duplicate.

PREPARATIVE EXAMPLE B
Preparation of the βGal(1→3/4) βGlcNAc α(1→3/4) fucosyltransferase from Human Milk (EC 2.4.1.65)

The enzyme was purified from human milk obtained from Lewis$^{a+b-}$ donors, according to the methodology using affinity chromatography on GDP-hexanolamine Sepharose described by Palcic et al.[22].

Fucosyltransferase Kinetics

Fucosyltransferase kinetics were performed as reported by Palcic et al.[22] Incubation mixtures contained (in 50 μL) 10 μM GDP-[$^{14}$C]-fucose (Amersham) (25,000 c.p.m.), 2 mM acceptor saccharide, 10 μU fucosyltransferase, 8 mM $MnCl_2$ in 25 mM sodium cacodylate buffer (pH 6.5). After 20 min. of incubation at 37° C., the reaction was terminated by addition of 1.0 mL of 35 mM EDTA and the radiolabelled products were separated by the Sep-Pak method[60]. Less than 20% of the GDP-[$^{14}$C]-fucose was transferred to the product. Initial rates are expressed as a percentage with respect to the value obtained with βGal(1→3)βGlcNAc-OR for the type I modified acceptors.

EXAMPLE 1
Synthesis of the starting material/Synthesis of Acceptors: Compounds 20b, 20c, 22b, 22c, 22d (FIG. 4)

A. Preparation of 8-Methoxycarbonyl 2,3,4,6-tetra O-acetyl-β-D-galactopyranosyl-(1→3)-O-2-azido-2-deoxy-β-D-glucopyranoside (compound 19) and 8-methoxycarbonyl 2,3,4,6-tetra-O-acetyl-β-D-galactopyranosyl-(1→4)-O-2-azido-2-deoxy-β-D glucopyranoside (compound 21).

A solution of trimethylsilyltrifluoromethanesulfonate (0.460 g, 1.94 mmol) in dry methylene chloride (5 mL) was syringed dropwise to a mixture of compound 17[35] (1.20 g, 1.94 mmol), compound 18 (0.757 g, 1.94 mmol) and molecular sieves 4A° (2 g) in dichloromethane stirred at 22° C. After 2 h, the reaction was stopped by addition of triethylamine, the mixture filtered and worked up as usual. The recovered material was chromatographed on silica gel (150 g) using a 3:1 mixture of hexanes and ethyl acetate as eluant providing a mixture of the β(1→3) and the β(1→4) disaccharide (1.10 g, 60%) which could not be separated at this stage.

Tetraethylammonium chloride (0.196 g, 1.18 mmol) and anhydrous potassium fluoride (0.299 g, 5.15 mmol) were added to a solution of the mixture of the above disaccharides (0.460 g, 0.487 mmol) in dry acetonitrile (10 mL). After 24 h at 22° C., acetic acid (1–5 mL) was added and the solvents were evaporated in vacuo. The residue was dissolved in chloroform (20 mL), washed with a dilute solution of sodium bicarbonate followed by water. The recovered crude material was chromatographed on silica gel (36 g) using a 1:1 mixture of ethyl acetate and hexane as eluant providing the (1→4) disaccharide 21 (157 mg, 46%) and the (1→3) disaccharide 19 (96 mg, 28%).

Disaccharide 21: $[α]_D^{20}$ +6.9°(c 1.0, $CHCl_3$) $^1$H-n.m.r. ($CDCl_3$) 5.381 (d, 1H, $J_{3',4'}$ 3.5 Hz, H-4'), 5.222(dd, 1H, $J_{1',2'}$ 8.0 Hz, $J_{2',3'}$ 10.0 Hz,H-2'), 5.014 (dd, 1H, H-3'), 4.628(d, 1H, H-1'), 4.257[m, incl. H-1 (d, $J_{1,2}$ 8.0 Hz)], 3.420–3.640 [m, incl. $CO_2CH_3$(s, 3.650)], 2.227(t,2H, J 7.5 Hz, $CH_2CO_2$), 2.150, 2.100 (two), 1.950(3s, 12H, 4 OAc), 1.600(m, 4H, methylenes), 1.300(m, 8H, methylenes);

Disaccharide 19: $[α]_D^{20}$ +7.8°(c 1, $CHCl_3$) $^1$H-n.m.r. ($CDCl_3$) 5.359 (d,1H, $J_{3',4'}$ 3.2 Hz), 5.225(dd, 1H, $J_{1',2'}$ 8.0, $J_{2',3'}$ 10 Hz, H-2'), 5.013 (dd, 1H, H-3'), 4.524 (d, 1H, H-1'), 4.300 (d, $J_{1,2}$ 8.0 Hz, H-1), 3.628(s, 3H, $CO_2CH_3$), 2.150, 2.080, 2.000, 1.920 (4s, 12H, 4 OAc), 1.600(m, 4H, methylenes), 1.300(m, 8H, methylenes).

For identification purposes both disaccharides were per-acetylated in a mixture of pyridine and acetic anhydride.

Peracetylated derivative of 21: 5.314(dd, 1H, $J_{3',4'}$ 3.5, $J_{4',5'}$ <1 Hz,H-4'), 5.047(dd, 1H, $J_{1',2'}$ 8.0, $J_{2',3'}$ 10.0 Hz, H-2'), 4.870–4.970[m,2H, incl. H-3, 4.923(dd, $J_{2',3'}$~$J_{3',4'}$ 10.0 Hz) and H-3'(4.903, dd)], 4.420[m, 2H, incl. H-1'(d)], 4.300(d, $J_{1,2}$ 8.0 Hz, H-1), 3.627[m, incl. $CO_2CH_3$(s, 3.627)], 3.335 (dd, 1H, H-2), 2.230(t,J 7.5 Hz, $CH_2CO_2$) 2.080, 2.070, 2.050, 2.010, 1.980, 1.936(5s, 18H, 6 OAc), 1.570(m, 4H, methylenes), 1.210(m, 8H, methylenes).

Peracetylated derivative of compound 19: 5.120(dd, 1H, $J_{3',4'}$ 3.5, $J_{4',5'}$ 1.0 Hz, H-4'), 5.080 (dd, 1H, $J_{1',2'}$ 7.8, $J_{2',3'}$ 10.0 Hz, H-2'), 4.980 (dd, 1H, H-3'), 4.875(dd, 1H, $J_{3,4}$~$J_{4,5}$~10.0 Hz, H-4), 4.715(d, 1H, H-1'), 4.257(d, 1H, $J_{1,2}$ 8.0 Hz, H-1), 3.627(s, 3H, $CO_2CH_3$), 3.320(dd, 1H, $J_{2,3}$ 10.0 Hz, H-2), 2.230(t, J 7.5 Hz, $CH_2CO_2$), 2.080, 2.050, 2.020, 2.010, 1.970, (6s, 18H, 6 OAc), 1.600(m, 4H, methylenes), 1.250 (m, 8H, methylenes).

B. Preparation of 8-Methoxycarbonyloctyl β-D-galactopyranosyl-(1–3)-O-2-azido-2-deoxy-β-D glucopyranoside (compound 20b)

A catalytic amount of a dilute solution of sodium methoxide in methanol was added to a solution of compound 19 (0.045 g, 0.064 mmol) in methanol (2 mL). After 5 h at 22° C., neutralization with Dowex 50W×8 ($H^+$ form) and filtration, the solvent was evaporated in vacuo providing the pure 20b (30 mg, 88%); $[β]_D^{20}$ −11.7°(c 0.65, $H_2O$) $^1$H-n.m.r. ($CD_3OD$,DOH: 4.80): δ4.45(d, 1H, J 7.0 Hz) and 4.34(d, 1H, J 7.5 Hz): H-1 and H-1', 3.61(s, $CO_2CH_3$), 2.27(t, 2H, J 7.5 Hz, $CH_2CO_2$), 1.58(m, 4H) and 1.30 (m, 8H): methylenes.

C. Preparation of 8-Methoxycarbonyloctyl β-D-galactopyranosyl-(1→3)-O-2-amino-2-deoxy-β-D glucopyranoside (compound 20c)

Compound 20b (0.018 g, 0.034 mmol) was hydrogenated in the presence of 5% palladium on carbon (5 mg) in methanol (2 mL) at atmospheric pressure for 6 h. After filtration through Celite, the solvent was evaporated and the residue chromatographed on Iatrobeads (2 g) using a mixture of chloroform and methanol as the eluant providing the pure compound 20c; $[α]^{20}_D$ −4.2° (c 0.48 $H_2O$); $^1$H-n.m.r. ($D_2O$, DOH at 4.80): δ4.56 and 4.48(2d, 1H each, J 7.5 Hz):

H-1 and H-1', 3.70(s, CO$_2$CH$_3$), 2.90(~t, 1H, J 9.5 Hz, H-2), 2.39(t, 2H, J 7.5 Hz, CH$_2$CO$_2$), 1.62(m, 4H) and 1.35 (m, 8H): methylenes.

D. Preparation of 8-Methoxycarbonyloctyl β-D-galactopyranosyl-(1→4)-O-2-azido-2-deoxy-β-D-glucopyranoside (compound 22b)

A catalytic amount of a dilute solution of sodium methoxide in methanol was added to a solution of compound 21 (0.027 g, 0.38 mmol) in methanol (2 mL). After 5 h at 22° C., neutralization with Dowex 50W×8 (H$^+$ form) and filtration, the solvent was evaporated in vacuo. The residue was chromatographed on Iatrobeads using a 65:35 mixture of chloroform and methanol as eluant to give compound 22b (0.019 g, 92%); $[\alpha]^{20}_D$ –12.4° (c 0.73 CH$_3$OH); $^1$H-n.m.r. (CD$_3$OD, DOH at 4.80): δ4.32(d, 1H, J 7.5 Hz) and 4.30 (d,1H, J 8.0 Hz): H-1 and H-1', 3.60(s, CO$_2$CH$_3$), 3.13(dd, J$_{1,2}$ 8.0 J$_{2,3}$ 10.0 Hz, H-2) 2.27(t, 2H, J 7.5 Hz, CH$_2$CO$_2$), 1.56(m, 4H) and 1.29(m, 8H): methylenes.

E. Preparation of 8-Methoxycarbonyloctyl β-D-galactopyranosyl-(1–4)-O-2-amino-2-deoxy-β-D-glucopyranoside (compound 22c)

Compound 22b (0.016 g, 0.29 mmol) was hydrogenated in the presence of 5% palladium on carbon (10 mg) in methanol (5 mL) for 5 h at 22° C. After filtration through Celite, the solvent was evaporated and the residue chromatographed on Iatrobeads (0.25 g) using a 8:2 mixture of chloroform and methanol as eluant providing the pure 22c (0.013 g, 86%). $[\alpha]^{20}_D$ 2.8° (c 0.42, H$_2$O)

F. Preparation of 8-Methoxycarbonyloctyl β-D-galactopyranosyl-(1–4)-O-2-deoxy-2-propionamido-β-D-glucopyranoside (compound 22d)

Compound 21 (0.017 g, 0.032 mmol) was hydrogenated in the presence of 5% palladium on carbon (5 mg) in methanol (8 mL) at atmospheric pressure for 8 h. After filtration through Celite and evaporation of the solvent, the residue was dissolved in dry methanol (3 mL) containing some triethylamine (0.150 mL). Propionic anhydride (0.150 mL) was added and the mixture was stirred for 4 h at 22° C. after which the solvents were evaporated to dryness. The residue was acetylated in a 2:1 mixture of pyridine and acetic anhydride (4 mL) at 22° C. for 18 h. After addition of methanol, the mixture was worked up as usual and after evaporation of the solvents, the residue was chromatographed on silica gel using a 1:1 mixture of ethyl acetate and hexane as eluant providing the pure hexa-O-acetate of compound 22d; $^1$H-n.m.r. (CDCl$_3$): 5.50(d, 1H, J 9.5 Hz, NH), 5.32(~d, J$_{3',4'}$ 3.5 Hz, H-4'), 5.07(m, 2H, H-2' and H-3), 4.93(dd, 1H, J$_{2',3'}$ 10.0 Hz, H-3'), 4.45(m, 3H, incl. H-1 and H-1'), 3.63(s, CO$_2$CH$_3$), 2.257(t, 2H, J 7.5, CH$_2$CO$_2$), 2.137 (dq, J 1.0 and 7.5 Hz, NHCH$_2$), 2.11, 2.07, 2.02 (three), 1.93(4s, 12H, 6 OAc), 1.540(m, 4H) and 1.25(m, 8H): methylenes, 1.09 (t, 2H, NHCH$_2$CH$_3$).

The above disaccharide was de-O-acetylated in dry methanol (1 mL) containing a catalytic amount of a solution of sodium methoxide. After neutralization with Dowex 50W×8 (H$^+$ form) resin and filtration, evaporation of the solvents left the pure 22d; $[\alpha]^{20}_D$ –18.0° (c 0.43, CH$_3$OH); $^1$H-n.m.r. (CD$_3$OD, DOH at 4.80): δ4.36(d, 1H, J 8.0 Hz) and 4.33(d, 1H, J 7.5 Hz): H-1 and H-1', 3.60(s, CO$_2$CH$_3$), 2.26(t, 2H, J 7.5 Hz, CH$_2$CO$_2$), 2.18(q, 2H, J 7.5 Hz, NHCOCH$_2$), 1.51(m, 4H) and 1.26(m, 8H): methylenes, 1.09(t, 3H, NHCOCH$_2$CH$_3$).

EXAMPLE 2

Synthesis of Acceptor 14a

A. Preparation of 8-Methoxycarbonyloctyl β-D-galactopyranosyl-(1→3)-O-2-acetamido-6-bromo 2,6-dideoxy-β-D-glucopyranoside (compound 14a)

A mixture of the compound 13[51] (0.061 g, 0.075 mmol), barium carbonate (0.020 g, 0.1 mmol) and N-bromosuccinimide (0.016 g, 0.09 mmol) in carbon tetrachloride (2 mL) was refluxed for 2 h as indicated[63]. After the appropriate work up, the recovered crude material was chromatographed on silica gel (6 g) using a 1:1 mixture of hexanes and ethyl acetate as eluant providing the pure bromo derivative (36 mg, 54%).

Some of this material (0.019 g, 0.021 mmol) in dry methanol was de-O-acetylated using a catalytic amount of sodium methoxide for 3 h at 22° C. After neutralization with Dowex 50W×8 (H$^+$ form) and filtration, the solvents were evaporated in vacuo and the residue chromatographed on Iatrobeads (2 g) using a 10:1 mixture of chloroform and methanol as eluant providing a pure disaccharide (0.012 g, 99%), which was poorly soluble in water. This material was saponified using a 0.25N solution of sodium hydroxyde for 1 h at 22° C. After neutralization with Dowex 50W×8 (H$^+$ form) and filtration, the solution was freeze dried in vacuo providing the disaccharide 14a; $[\alpha]^{20}_D$ –11.4° (c 0.12, H$_2$O).

EXAMPLE 3

Synthesis of Sialylated Trisaccharides (Compounds 7b, 7c, and 7d)

A. Preparation of 8-methoxycarbonyloctyl (5-acetamido-3,5-dideoxy-D-glycero-α-D-galacto-2-nonulopyranosylonic acid)-(2→3)-O-(β-D-galactopyranosyl)-(1→3)-O-(2-azido-2-deoxy-β-D-glucopyranoside (Trisaccharide 7b)

Trisaccharide 3 (60.8 mg, 0.05 mmol) was hydrogenated in ethyl acetate (1.5 mL) at 22° C. in the presence of 5% palladium on carbon (60 mg) for 1 h to obtain the intermediate free acid (57.6 mg, 98.8%), $[\alpha]_D$ –14.7° (c, 0.18, chloroform); i.r. (chloroform): 2120 cm$^{-1}$ (N$_3$). This intermediate was de-O-acetylated by using a catalytic amount of sodium methoxide in methanol for 16 h at 22° C. After neutralization with BioRex-70 (BioRad) weak acid resin (H$^+$ form) and evaporation of the filtrate, the residue was chromatographed on BioGel P2 providing trisaccharide 7b (36.6 mg. 88%), $[\alpha]_D$ –10.1° (C,0.32, water). $^1$H-n.m.r. data are reported in Table II.

B. Preparation of 8-methoxycarbonyloctyl (benzyl-5-acetamido-4,7,8,9-tetra-O-acetyl-3,5-dideoxy D-glycero-α-D-galacto-2-nonulopyranosylonate)-(2→3) -O-(2,4,6-tri-O-acetyl-β-D-galactopyranosyl)-(1→3)-O-(6-O-acetyl-2-amino-2-deoxy-β-D-glucopyranoside) (trisaccharide 5)

Hydrogen sulfide was bubbled through a solution of trisaccharide 3 (500 mg, 0.4 mmol) in a mixture of pyridine (40 mL), water (6 mL) and triethylamine (1.5 mL). After 16 h at 22° C., the mixture was evaporated to dryness and co-evaporated with toluene to give a crude product (450 mg). Some of this material (105 mg) was chromatographed (10:1, toluene-ethanol) providing tetrasaccharide 5 (86 mg, 75%), $[\alpha]_D^{20}$ –21.1°(c,0.02, chloroform). $^1$H-n.m.r. (CDCl$_3$): δ7.32–7.45(m, 5H, aromatics), 5.484(ddd, 1H, J$_{7'',8''}$8.5, J$_{8'',9''a}$ 2.5, J$_{8'',9''b}$ 5.5 Hz,H-8''), 5.418(d, 1H, J 12.2 Hz, benzylic), 5.291(dd, 1H, J$_{6'',7''}$ 2.7 Hz, H-7''), 5.080(dd, 1H, J$_{1',2'}$ 8.0, J$_{2',3'}$ 10.0 Hz, H-2'), 5.022(d, 1H, J 12.2 Hz, benzylic), 4.980(bd, 1H, J$_{3',4'}$ 3.5 Hz, H-4'), 4.890(d, 1H, J$_{5'',NH}$ 10.5 Hz, NH), 4.829(ddd,1H, J$_{3''eq,4''}$4.5, J$_{3''ax,4''}$12.5, J$_{4'',5''}$ 10.5 Hz,H-4''), 4.739(d, 1H, J$_{1',2'}$ 8.0 Hz, H-1'), 4.670 (dd, 1H, J$_{2',3'}$ 10.3, J$_{3',4'}$ 3.5 Hz, H-3'), 3.635(s, 3H, OCH$_3$), 2.851(dd, 1H, J$_{1,2}$ 8.5, J$_{2,3}$ 9.5 Hz, H-2), 2.586(dd, 1H, J$_{3''ax,3''eq}$ 13.0 Hz, H-3''eq), 2.265(t, 1H, 7.5 Hz, CH$_2$CO$_2$), 2.222, 2.150, 2.060, 2.050, 2.045, 2.040, 2.018, 1.958, 1.805(9 s, 3H each, 8 OAc, 1 NHAc), 1.650(t, 1H, H-3''ax) 3-H''ax), 1.564(m, 6H, methylenes), 1.300(m, 8H, methylenes).

C. Preparation of 8-methoxycarbonyloctyl (5-acetamido-3,5-dideoxy-D-glycero-α-D-galacto-2-nonulopyranosylonic acid)-(2→3)-O-(β-D-galactopyranosyl)-(1→3)-O-(2-amino-2-deoxy-β-D-glucopyranoside (tetrasaccharide 7c)

A solution of pure trisaccharide 5 (82 mg, 0.07 mmol) in methanol (1 mL) was hydrogenated for 1 h at 22° C. in the presence of 5% palladium on carbon (82 mg). Filtration of the catalyst and evaporation left the intermediate (76 mg), $[\alpha]_D^{20}$ +6.0° (c,0.4, chloroform). This compound (72 mg, 0.06 mmol) was de-O-acetylated by using a catalytic amount of sodium methoxide in methanol (3 mL) for 24 h at 22° C. Evaporation of the solution obtained after neutralization with acetic acid left a material which was purified by chromatography on BioGel P2 providing trisaccharide 7c (45.5 mg) 88%, $[\alpha]_D$ −6.30° (c,0.35, water). $^1$H-n.m.r. data are reported in Table II.

D. 8-Methoxycarbonyloctyl (benzyl-5-acetamido-4,7,8,9-tetra-O-acetyl-3,5-dideoxy-D-glycero-α-D-galacto-2-nonulopyranosylonate)-(2→3)-O-(2,4,6-tri-O-acetyl-β-D-galactopyranosyl)-(1→3)-O-(6-O-acetyl-2-deoxy-2-N-propionamido-β-D-glucopyranoside) (trisaccharide 6)

Propionic anhydride (0.5 mL) was added dropwise in 10 min to a solution of the crude amino trisaccharide 5 (140 mg, 0.11 mmol) in a mixture of pyridine (9.5 mL) and water 0.9 mL). The mixture was stirred overnight at 22° C., evaporated in vacuo and co-evaporated with toluene leaving a residue which was chromatographed (100:10, toluene:ethanol) providing trisaccharide 6 (110 mg, 72%) which contained a small amount of the 4-O-propionylated trisaccharide. $^1$H-n.m.r. (CDCl$_3$): δ7.310–7.450(m, 5H, aromatics), 5.812(d, 1H, J 8.0 Hz, NH), 5.450[m, incl., H-8" and benzylic (d, J 12.5 Hz)], 5.280(dd), $J_{6",7"}$ 2.7, $J_{7",8"}$ 8.5 Hz, H-7"), 5.300[m, incl. benzylic (d)], 3.630(s, 3H, OCH$_3$), 2.578(dd, 1H, $J_{3"eq,3"ax}$ 13.0 Hz, H-3"eq), 2.262(t, 2H, J 7.5 Hz, CH$_2$CO$_2$), 2.200(q,NHCOCH$_2$), 2.147, 2.060, 2.045 (five), 1.955, 1.800(5s, 27H, 8 OAc, 1 NAc), 1.630(t, 1H, $J_{3"ax,4"}$ 13.0 Hz, H-3"), 1.570(m, 6H, methylenes), 1.240(m, 8H, methylenes), 1.130(t, 7.5 Hz, COCH$_2$CH$_3$).

E. Preparation of 8-methoxycarbonyloctyl (5-acetamido-3,5-dideoxy-D-glycero-α-D-galacto-2-nonulopyranosylonic acid)-(2→3)-O-β-D-galactopyranosyl-(1→3)-O-(2-deoxy-2-N-propionamido-(β-D-glucopyranoside (trisaccharide 7d)

Trisaccharide 6 (105 mg, 0.082 mmol) was deprotected using the same procedure as indicated in the synthesis of 7c. Chromatography on BioGel P2 providd the pure 7d (60.8 mg, 95%), $[\alpha]_D^{20}$ −16.6° (c,0.32, water). $^1$H-n.m.r. data are reported in Table II.

EXAMPLE 4
Preparative Fucosylation
  i. Synthesis of GDP-Fucose.
  A. Preparation of Bis(tetra-n-butylammonium) hydrogen phosphate Tetra-n-butylammonium hydroxide (40% aq. w/w, about 150 g) was added dropwise to a solution of phosphoric acid (85% aq, w/w, 18 g, 0.155 mmol) in water (150 mL) until the pH reached 7. Water was then evaporated in vacuo to give a syrup which was co-evaporated with dry acetonitrile (2×400 mL) followed by dry toluene (2×400 mL). The resulting white solid (75 g) was dried in vacuo and stored over phosphorus pentoxide under vacuum until used.

B. Preparation of β-L-Fucopyranosyl-1-phosphate

A solution of bis(tetra-n-butylammonium) hydrogen phosphate (58 g, 127.8 mmol) in dry acetonitrile (300 mL) was stirred at room temperature under nitrogen in the presence of molecular sieves (4 Å, 20 g) for about one hour. A solution of tri-O-acetyl fucosyl-1-bromide (freshly prepared from 31 g, 93 mmol of L-fucose tetraacetate in the manner of Nunez et al.[65]) in dry toluene (100 mL) was added dropwise in about 0.5 hour to the above solution, cooled at 0° C. After one more hour at 0° C., the mixture was brought to room temperature and stirred for 3 hour. Tlc (1:1 toluene:ethyl acetate) indicated a main spot on the base line and several faster moving smaller spots.

The mixture was filtered over a pad of Celite (which was further washed with acetonitrile) and the solvents evaporated in vacuo to give a red syrup. This material was dissolved in water (400 mL) and extracted with ethyl acetate (250 mL, twice). The aqueous layer was then evaporated in vacuo leaving a yellowish syrup to which a solution of ammonium hydroxide (25% aq., 200 mL) was added. The mixture was stirred at room temperature for 3 hours after which tlc (65:35:8 chloroform:methanol:water) indicated a baseline spot. The solvent was evaporated in vacuo to give a yellowish syrup which was diluted with water (400 mL). The pH of this solution was checked and brought to 7, if necessary, by addition of a small amount of hydrochloric acid. The solution was slowly absorbed onto a column of ion exchange resin Dowex 2×8 [200–400 mesh, 5×45 cm, bicarbonate form which had been prepared by sequential washing of the resin with methanol (800 mL), water (1200 mL), ammonium bicarbonate (1M, 1600 mL) and water (1200 mL)]. Water (1000 mL) was then run through the column followed by a solution of ammonium bicarbonate (0.5M, 2.3 mL/minute, overnight). The eluate was collected in fractions (15 mL) and the product detected by charring after spotting on a tlc plate. Fractions 20 to 57 were pooled and evaporated in vacuo leaving a white solid which was further co-evaporated with water (3×300 mL) and freeze drying of the last 50 mL and then drying of the residue with a vacuum pump to give β-L-fucopyransyl-1-phosphate (9.5 g, 40%) as a 12:1 mixture of β and α anomers containing some ammonium acetate identified by a singlet at δ=1.940 in the $^1$H-n.m.r. spectrum. This product was slowly run through a column of Dowex 5×8 resin (100–200 mesh, triethylammonium form) and eluted with water to provide the bis triethylammonium salt of β-L-fucopyransyl-1-phosphate as a sticky gum after freeze drying of the eluate. $^1$H-n.m.r. (FIG. 1) δ:4.840 (dd, $J_{1,2}$=$J_{1,P}$=7.5 Hz, H-1), 3.82 (q, 1H, $J_{5,6}$ 6.5 Hz, H-5), 3.750 (dd, 1H, $J_{3,4}$ 3.5, $J_{4,5}$ 1.0 Hz, H-4), 3.679 (dd, 1H, $J_{2,3}$ 10.0 Hz, H-3), 3.520 (dd, 1H, H-2), 1.940 (s, acetate), 1.26 (d, H-6). Integral of the signals at 3.20 (q, J 7.4 Hz, NCH$_2$) and 1.280 and 1.260 (NCH$_2$CH$_3$ and H-6) indicates that the product is the bis-triethylammonium salt which may loose some triethylamine upon extensive drying. $^{13}$C-n.m.r. δ:98.3 (d, $J_{C,1P}$ 3.4 Hz, C-1), 72.8 (d, $J_{C,2P}$ 7.5 Hz, C-2), 16.4(C-6); $^{31}$P-nmr δ: +2.6(s).

β-L-fucopyransyl-1-phosphate appears to slowly degrade upon prolonged storage (1+ days) in water at 22° C. and, accordingly, the material should not be left, handled or stored as an aqueous solution at 22° C. or higher temperatures. In the present case, this material was kept at −18° C. and dried in vacuo over phosphorus pentoxide prior to being used in the next step.

C. Preparation of Guanosine 5'-(β-1-fucopyranosyl)-diphosphate

Guanosine 5'-(β-1-fucopyranosyl)-diphosphate was prepared from β-L-fucopyranosyl-1-phosphate using two different art recognized procedures as set forth below:
PROCEDURE #1
β-L-fucopyranosyl-1-phosphate and guanosine 5'-monophosphomorpholidate (4-morpholine-N,N'-dicyclohexyl-carboxamidine salt, available from Sigma, St. Louis, Mo., "GMP-morpholidate") were reacted as described in a recent modification[64,66] of Nunez's original procedure[65]. Accordingly, tri-n-octylamine (0.800 g, available from Aldrich Chemical Company, Milwaukee, Wis.)

was added to a mixture of β-L-fucopyranosyl-1-phosphate (triethyl-ammonium salt, 1.00 g, about 2.20 mmol) in dry pyridine (10 mL) under nitrogen the solvent removed in vacuo. The process was repeated three times with care to allow only dry air to enter the flask. GMP morpholidate (2.4 g, about 3.30 mmol) was dissolved in a 1:1 mixture of dry dimethylformamide and pyridine (10 mL). The solvents were evaporated in vacuo and the procedure repeated three times as above. The residue was dissolved in the same mixture of solvents (20 mL) and the solution added to the reaction flask accompanied by crushed molecular sieves (2 g, 4 Å). The mixture was stirred at room temperature under nitrogen. Tlc (3:5:2 25% aq. ammonium hydroxide, isopropanol and water) showed spots corresponding to the starting GMP-morpholidate (Rf~0.8, U.V.), guanosine 5'-(β-1-fucopyranosyl)-diphosphate (Rf~0.5, U.V. and charring), followed by the tailing spot of the starting fucose-1-phosphate (Rf~0.44, charring). Additional U.V. active minor spots were also present. After stirring for 4 days at room temperature, the yellowish mixture was co-evaporated in vacuo with toluene and the yellowish residue further dried overnight at the vacuum pump leaving a thick residue (2.43 g). Water (10 mL) was then added into the flask to give a yellow cloudy solution which was added on top of a column of AG 50W-X12 (from Biorad) resin (100–200 mesh, 25×1.5 cm, Na$^+$ form). The product eluted with water after the void volume. The fractions which were active, both by U.V. and charring after spotting on a tlc plate, were recovered and the solution freeze-dried overnight in vacuo providing a crude material (1.96 g).

This residue was dissolved in water (10 mL overall) and slowly absorbed onto a column of hydrophobic $C_{18}$ silica gel (Waters, 2.5×30 cm) which had been conditioned by washing with water, methanol and water (250 mL each). Water was then run through the column (0.4 mL/min) and the eluate collected in fractions (0.8 mL) which were checked by tlc (3:5:2 25% aq. ammonium hydroxide, isopropanol and water). β-L-fucopyranosyl-1-phosphate, (Rf~0.54, charring) was eluted in fractions 29 to 45. A product showing a strongly U.V. active spot (Rf~0.51) eluted mainly in fractions 46 to 65. Other minor U.V. active spots of higher or lower Rf were observed. Fractions 59 to 86, which contained guanosine 5'-(β-1-fucopyranosyl)-diphosphate (Rf~0.62), also showed a narrow U.V. active spot (Rf~0.57). Fractions 59 to 86 were pooled and freeze-dried overnight providing 0.353 g of material enriched in guanosine 5'-(β-1-fucopyranosyl)-diphosphate. $^1$H-n.m.r. indicated that this material was contaminated by a small amount of impurities giving signals at δ=4.12 and δ=5.05.

Fractions 29 to 45 and 47 to 57 were separately pooled and freeze-dried providing recovered β-L-fucopyranosyl-1-phosphate (0.264 g and 0.223 g, respectively, in which the second fraction contains some impurities). Occasionally, pooling of appropriate fractions provided some amount of guanosine 5'-(β-1-fucopyranosyl)-diphosphate in good purity ($^1$H-n.m.r.). Generally, all the material enriched in guanosine 5'-(β-1-fucopyranosyl)-diphosphate was dissolved in a minimum amount of water and run on the same column which had been regenerated by washing with large amounts of methanol followed by water. The fractions containing the purified guanosine 5'-(β-1-fucopyranosyl)-diphosphate (tlc) were pooled and freezed dried in vacuo leaving a white fluffy material (187 mg, 16%). $^1$H-n.m.r. (FIG. 2) was identical to the previously reported data[55].

PROCEDURE #2

β-L-fucopyranosyl-1-phosphate and guanosine 5'-monophosphomorpholidate (4-morpholine-N,N'-dicyclohexylcarboxamidine salt—"GMP-morpholidate") were reacted in dry pyridine as indicated in the original procedure[65]. Accordingly, the β-L-fucopyranosyl-1-phosphate (triethyl-ammonium salt, 0.528 g, about 1.18 mmol) was dissolved in dry pyridine (20 mL) and the solvent removed in vacuo. The process was repeated three times with care to allow only dry air to enter the flask. GMP-morpholidate (1.2 g, 1.65 mmol) and pyridine (20 mL) were added into the reaction flask, the solvent evaporated in vacuo and the process repeated three times as above. Pyridine (20 mL) was added to the final residue and the heterogeneous mixture was stirred for 3 to 4 days at room temperature under nitrogen. An insoluble mass was formed which had to be occasionally broken down by sonication.

The reaction was followed by tlc and worked up as indicated in the first procedure to provide the GDP-fucose (120 mg, 16%).

ii. Enzymatic Conditions

βGal(1→3/4)βGlcNAc(1→3/4) fucosyltransferase was purified from human milk according to the methodology using affinity chromatography on GDP-hexanolamine Sepharose described by Palcic et al .[22] The enzymatic reactions were carried out at 37° C. in a plastic tube using a sodium cacodylate buffer (100 mM, pH 6.5), $MnCl_2$ (10 mM), ATP (1.6 mM) $NaN_3$ (1.6 mM). The final reaction mixture was diluted with $H_2O$ (5 mL) and applied onto $C_{18}$ Sep-Pak cartridges as reported[22]. After washing with $H_2O$ (30 mL) the products were eluted with $CH_3OH$ and the solvents evaporated. The residue was dissolved in a 65:35:5 mixture of $CHCl_3$, $CH_3OH$, and $H_2O$ and applied on a small column of Iatrobeads (0.200 to 0.500 g). After washing with the same solvent mixture, the products were eluted with a 65:35:8 and/or 60:40:10 mixtures of the same solvents. The appropriate fractions (t.l.c.) were pooled, the solvents evaporated in vacuo, the residue run through a small column of AG 50W×8 (Na$^+$ form) (BioRad) in $H_2O$ and the products recovered after freeze drying in vacuo. $^1$H-n.m.r. data of the tetrasaccharides are reported in Table II above.

iii. Fucosylation Reactions

A. Preparation of 8-methoxycarbonyloctyl (5-acet amido-3, 5-di-deoxy-D-glycero-α-D-galacto-2-nonulopyranosylonic acid)-(2→3)-O-β-D-galactopyranosyl-(1→3)-O-[α-L-fucopyranosyl-(1→4)-O]-(2-azido-2-deoxy-β-D-glucopyranoside) (Tetrasaccharide 8b)

The trisaccharide 7b (8.7 mg), GDP-fucose (18 mg), the fucosyltransferase (18 mU) and calf intestine alkaline phosphatase (10 U) were incubated for 68 h in the buffer (2 mL). Isolation and purification provided tetrasaccharide 8b (4.42 mg).

B. Preparation of 8-Methoxycarbonyloctyl (5-acetamido-3, 5-di-deoxy-D-glycero-α-D-galacto-2-nonulopyranosylonic acid)-(2→3)-O-β-D-galacto-pyranosyl-(1→3)-O-[α-L-fucopyranosyl-(1→4)-O]-(2-amino-2-deoxy-β-D-glucopyranoside) (tetrasaccharide 8c)

The trisaccharide 7c (9.5 mg), GDP-fucose (18 mg), the fucosyltransferase (18 mU) and calf intestine alkaline phosphatase (10 U) were incubated for 60 h in the buffer (2.8 mL). Isolation and purification provided for tetrasaccharide 8c (4.94 mg).

C. Preparation of 8-methoxycarbonyloctyl(5-acetamido-3,5-di-deoxy-D-glycero-α-D-galacto-2-nonulopyranosylonic acid)-(2→3)-O-β-D-galacto-pyranosyl-(1→3)-O-[α-L-fucopyranosyl-(1→4)-O]-(2-N-propionamido-2-deoxy-β-D-glucopyranoside) (tetrasaccharide 8d)

Trisaccharide 7d (8.4 mg), GDP-fucose (18 mg), the fucosyltransferase (19.4 mU) and calf intestine alkaline phosphatase (10 U) were incubated for 72 h in the buffer (2 mL). Isolation and purification provided for tetrasaccharide 8d (5.81 mg).

EXAMPLE 5

Synthesis of Artificial Antigens

Sialyl Lewis$^a$ analogues containing an appropriate functional group in the glycoside moiety can be conjugated to antigenic carriers containing one or more complementary functional groups following procedures known in the art. Depending on the linking chemistry employed, the sialyl and fucosyl groups can be included in the saccharide to be conjugated or, a βGal(1→3)βGlcNAc derivative can be conjugated and the resulting conjugate sialylated and fucosylated to provide for sialyl Lewis$^a$ analogues.

Specifically, the conjugation of the disaccharide glycosides such as structure 14a to BSA, KLH or other carriers is achieved by procedures such as the "acyl-azide" procedure of Lemieux et al. and Pinto et al.[51,52]. The resulting conjugates are then sialylated and fucosylated in a manner similar to that reported above and the products purified by a combination of ultrafiltration and Gel-filtration to provide for artificial antigens having one or more sialyl Lewis$^a$ analogues attached thereto.

Similarly, other antigenic carriers can be used to create artificial antigens including KLH, human serum albumin (HSA), diphtheria or tetanus toxins, S-layers, and the like. Likewise, other derivatives of βGal(1→3)βGlcNAc could be conjugated (coupled) to the antigenic carriers used in place of compound 14a.

Alternatively, tetrasaccharide 8b can be directly conjugated to antigenic carriers containing one or more complementary functional groups following procedures known in the art. For example, the —(CH$_2$)$_n$CO$_2$CH$_3$ aglycon of tetrasaccharide 8b can be modified by reaction with hydrazine and N$_2$O$_4$ to convert the ester (COOCH$_3$) to an acyl azide (—C(O)N$_3$). The azide is then displaced by reaction with an amino functionality on the antigenic carrier resulting in linking of the alpha sialylated oligosaccharide glycoside to the carrier via an amide bond.

Because the carrier can contain numerous amine groups, the carrier is capable of adding more than one sialyl Lewis$^a$ derivatives.

EXAMPLE 6

Synthesis of Aggregates Containing Sialyl Lewis$^A$ Analogues

Aggregates such as liposomes and micelles can be prepared so as to incorporate sialyl Lewis$^a$ analogues. Specifically, incorporation of the sialyl Lewis$^a$ analogue into such aggregates requires that the aglycon moiety be sufficiently hydrophobic to be incorporated into such aggregates. It is contemplated that such hydrophobic aglycons can include the —(CH$_2$)$_2$COOCH$_3$ which has been extended by various moieties such as naphthyl, substituted naphthyl, octyl, and the like which would improve the ability to incorporate the saccharide into the aggregate.

In such aggregates, the hydrophobic aglycon group of the sialyl Lewis$^a$ analogue becomes partitioned in the lipid portion of the aggregate whereas the tetrasaccharide group is generally partitioned in the aqueous phase.

Methods of preparing such aggregates are well known in the art. See, for instance, U.S. Pat. No. 4,522,803 which is incorporated herein by reference.

Additionally, sialyl Lewis$^x$ analogues are disclosed in our concurrently filed application, Ser. No. 07/887,746, now abandoned in favor of Ser. No. 08/326,745, entitled "Modified Sialyl Lewis$^x$ Compounds". As noted above, that application is filed concurrently this application and is incorporated herein by reference in its entirety.

Now having fully described this invention, it will be understood by those with skill in the art that the invention may be practiced within a wide and equivalent range of conditions, parameters, and the like, without affecting the scope or spirit of the invention or any embodiment thereof.

Modifications of the above-described methods for carrying out the invention that are obvious to persons of skill in medicine, chemistry, biochemistry, immunology, and/or related fields are intended to be within the scope of the following claims.

What is claimed is:

1. A compound represented by Formula I:

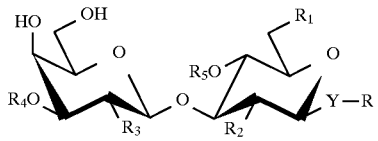

wherein R is selected from the group consisting of hydrogen and an aglycon having 1 to 10 carbon atoms;

R$_1$ is selected from the group consisting of hydrogen, —NH$_2$, N$_3$, —NHSO$_3$H, —NR$_8$C(O)R$_6$, [—N=C(R$_7$)$_2$,] —NHCH(R$_7$)$_2$, —N(R$_8$)$_2$, —SR$_8$, —O(C(O))$_p$R$_9$, fluoro, chloro, bromo and sulfate, wherein R$_6$ is selected from the group consisting of hydrogen,
alkyl of from 1 to 4 carbon atoms optionally substituted with 1 or more substituents selected from the group consisting of hydroxy, chloro, bromo, alkoxy of from 1 to 4 carbon atoms, phenyl, and phenyl substituted with 1 to 3 substituents selected from the group consisting of hydroxy, alkyl of from 1 to 4 carbon atoms, alkoxy of from 1 to 4 carbon atoms, chloro, bromo, and sulfate,
an amino acid or polypeptidyl residue,
—OR$_{10}$ wherein R$_{10}$ is alkyl of from 1 to 4 carbon atoms, or alkyl of from 2 to 4 carbon atoms substituted with a hydroxyl group, and
—NR$_{11}$R$_{12}$ wherein R$_{11}$ and R$_{12}$ are independently selected from the group consisting of hydrogen and alkyl of from 1 to 4 carbon atoms,
each R$_7$ is independently selected from the group consisting of hydrogen and alkyl of from 1 to 4 carbon atoms,
R$_8$ is independently selected from the group consisting of hydrogen and alkyl of from 1 to 4 carbon atoms,
R$_9$ is selected from the group consisting of hydrogen, alkyl of from 1 to 4 carbon atoms optionally substituted with 1 or more substituents selected from the group consisting of hydroxy, chloro, bromo, alkoxy of from 1 to 4 carbon atoms, phenyl, and phenyl substituted with 1 to 3 substituents selected from hydroxy, alkyl of from 1 to 4 carbon atoms, alkoxy of from 1 to 4 carbon atoms, chloro, bromo, and sulfate,
and p is an integer equal to 0 or 1;

R$_2$ is selected from the group consisting of hydrogen, —N$_3$, —NH$_2$, —NHSO$_3$H, —NR$_{15}$C(O)R$_{13}$, —N=C(R$_{14}$)$_2$, —NHCH(R$_{14}$)$_2$, —N(R$_{15}$)$_2$, —O(C(O))$_q$R$_{16}$, fluoro, chloro, and sulfate, wherein R$_{13}$ is selected from the group consisting of hydrogen,
alkyl of from 1 to 4 carbon atoms optionally substituted with 1 or more substituents selected from the group consisting of hydroxy, chloro, bromo, and alkoxy of from 1 to 4 carbon atoms,
an amino acid or polypeptidyl residue,
—OR$_{17}$ wherein R$_{17}$ is alkyl of from 1 to 4 carbon atoms, or alkyl of from 2 to 4 carbon atoms substituted with a hydroxyl group, and —$NR_{18}R_{19}$ wherein $R_{18}$ and $R_{19}$ are independently selected from the group consisting of hydrogen and alkyl of from 1 to 4 carbon atoms, each $R_{14}$ is independently selected from the group consisting of hydrogen and alkyl of from 1 to 4 carbon atoms, each $R_{15}$ is independently selected from the group consisting of hydrogen and alkyl of from 1 to 4 carbon atoms, $R_{16}$ is selected from the group consisting of hydrogen, alkyl of from 1 to 4 carbon atoms optionally substituted with from 1 to 4 carbon atoms substituted with 1 or more substituents selected from the group consisting of hydroxy, chloro, bromo, and alkoxy of from 1 to 4 carbon atoms, and q is an integer equal to 0 or 1;

$R_3$ is selected from the group consisting of hydrogen, fluoro, and hydroxy;

$R_4$ is sialyl;

$R_5$ is L-fucosyl;

Y is selected from the group consisting of O, S, —NH—, and a bond; or a pharmaceutically acceptable salt thereof and with the proviso that when $R_1$ is hydroxyl and $R_2$ is —$NHC(O)R_{13}$ wherein $R_{13}$ is alkyl of from 1 to 4 carbon atoms then $R_3$ is not hydroxy.

2. A compound of claim 1 wherein $R_3$ is hydroxyl.

3. A compound of claim 2 wherein $R_1$ is hydroxyl, alkoxy of from 1 to 4 carbon atoms, fluoro, chloro, or bromo.

4. A compound of claim 1 wherein $R_2$ is selected from the group consisting of —$NH_2$, —$NHC(O)R_{13}$, and —$N_3$ wherein $R_{13}$ is as defined in claim 1.

5. A compound of claim 1 wherein $R_4$ is Neu5Ac.

6. A compound of claim 1 wherein $R_5$ is L-fucose.

7. A compound of claim 1 wherein $R_1$ is hydroxy, $R_2$ is azido, $R_3$ is hydroxy, $R_4$ is Neu5Ac, and $R_5$ is L-fucose.

8. A compound of claim 1 wherein $R_1$ is hydroxy, $R_2$ is —$NH_2$, $R_3$ is hydroxy, $R_4$ is Neu5Ac, and $R_5$ is L-fucose.

9. A compound of claim 1 wherein $R_1$ is chloro, $R_2$ is —$NHC(O)CH_3$, $R_3$ is hydroxy, $R_4$ is Neu5Ac, and $R_5$ is L-fucose.

10. A compound of claim 1 wherein $R_1$ is bromo, $R_2$ is —$NHC(O)CH_3$, $R_3$ is hydroxy, $R_4$ is Neu5Ac, and $R_5$ is L-fucose.

11. A compound of claim 1 wherein $R_1$ is fluoro, $R_2$ is —$NHC(O)CH_3$, $R_3$ is hydroxy, $R_4$ is Neu5Ac, and $R_5$ is L-fucose.

12. A pharmaceutical composition suitable for administration to a mammal which comprises a pharmaceutically inert carrier and an effective amount of the compound of claim 1 wherein $R_1$ and $R_3$ are hydroxyl, $R_4$ is sialyl and $R_2$ is selected from the group consisting of azido and amino to modulate a cell-mediated immune response in said mammal.

* * * * *